United States Patent
Weber

(10) Patent No.: US 7,220,972 B2
(45) Date of Patent: May 22, 2007

(54) METHOD AND APPARATUS FOR THE CHARACTERIZATION AND ANALYSIS OF THE SHAPE OF MOLECULES AND MOLECULAR CLUSTERS, AND FOR THE SEPARATION OF DESIRED ISOMERS, BASED ON RYDBERG STATES

(75) Inventor: Peter M. Weber, Barrington, RI (US)

(73) Assignee: Brown University, Providence, RI (US)

( * ) Notice: Subject to any disclaimer, the term of this patent is extended or adjusted under 35 U.S.C. 154(b) by 64 days.

(21) Appl. No.: 10/515,942

(22) PCT Filed: Mar. 24, 2003

(86) PCT No.: PCT/US03/08977

§ 371 (c)(1),
(2), (4) Date: Nov. 24, 2004

(87) PCT Pub. No.: WO03/102033

PCT Pub. Date: Dec. 11, 2003

(65) Prior Publication Data

US 2005/0230612 A1   Oct. 20, 2005

(51) Int. Cl.
*H01J 27/24* (2006.01)
(52) U.S. Cl. ............................... 250/423 P
(58) Field of Classification Search ............ 250/423 P
See application file for complete search history.

(56) References Cited

U.S. PATENT DOCUMENTS

| 3,897,302 A | 7/1975 | Klein | 176/86 |
| 3,987,302 A | 10/1976 | Hurst et al. | 250/283 |
| 4,107,537 A * | 8/1978 | Forsen et al. | 250/423 P |
| 4,360,501 A * | 11/1982 | Bir et al. | 204/157.22 |
| 6,008,496 A * | 12/1999 | Winefordner et al. | 250/423 P |

* cited by examiner

*Primary Examiner*—David Vanore
(74) *Attorney, Agent, or Firm*—Harrington & Smith, PC

(57) ABSTRACT

A method and apparatus to characterize a shape of an isomeric form of a sample comprised of a molecule or a cluster of molecules. The method includes raising an electron of the sample to a Rydberg state having an orbital diameter sufficient to encompass at least a portion of the sample; further raising the electron to an ionization state and correlating the energy required to transition from the Rydberg state to the ionization state with the three dimensional structure of the sample. In a preferred embodiment raising the electron to the Rydberg state includes raising the electron to a first Rydberg state $Ry_1$, and then raising the electron to a second Rydberg state $Ry_2$. Further raising the electron to the ionization state includes raising the electron from the $Ry_2$ state to the ionization state using optical excitation, and correlating the energy considers at least a wavelength of the optical excitation. Also disclosed are method and apparatus that use the Rydberg states to separate at least one isomeric form of a sample from other isomeric forms of the sample, where the sample is comprised of a molecule or a cluster of molecules.

73 Claims, 12 Drawing Sheets

| MOLECULE | QUANTUM DEFECT δ | |
|---|---|---|
| | S-STATES | P-STATES |
| PYRIMIDINE, 1,3-$C_4N_2H_4$ | 0.76 | 0.54, 0.58 |
| PYRIDAZINE, 1,2-$C_4N_2H_4$ | 0.99 | 0.59 |
| PYRAZINE, 1,4-$C_4N_2H_4$ | 0.98 | 0.58, 0.43 |
| 1,3,5-TRIAZINE, $C_3N_3H_3$ | 0.80 | 0.42 |
| 1,3,5-TRIAZINE, $C_3N_3H_3$ | 0.91 | 0.69, 0.60 |
| 1,2,3-TRIAZINE, $C_3N_3H_3$ | 0.95 | 0.53 |

$S_0 \xrightarrow{h\nu} S_2 \xrightarrow{h\nu} Ry_1$   FIG. 16A

$Ry_1 \xrightarrow{h\nu} Ry_2 \xrightarrow{h\nu} Ion$   FIG. 16B

$E_n = IP - \dfrac{Ry}{(n-\delta)^2}$   FIG. 16C

$S_0 \xrightarrow{h\nu} S_1 \xrightarrow{h\nu} S_n \longrightarrow Ry$   FIG. 16D

$Ry \xrightarrow{h\nu} Ion + e^-$   FIG. 16E

$E(Ry_2) - E(Ry_1) = f_1(\delta_1, \delta_2)$   FIG. 16F

$IP - E(Ry_2) = f_2(\delta_2)$   FIG. 16G

METHOD AND APPARATUS FOR THE CHARACTERIZATION AND ANALYSIS OF THE SHAPE OF MOLECULES AND MOLECULAR CLUSTERS, AND FOR THE SEPARATION OF DESIRED ISOMERS, BASED ON RYDBERG STATES

TECHNICAL FIELD

These teachings relate generally to methods and instrumentation for analyzing and for separating molecules and assemblages of molecules, such as metallic clusters, and more specifically to the analysis and separation of isomeric forms of molecules, such as proteins and other biological molecules, and constituents thereof such as amino acids, as well as isomeric forms of molecular clusters, such as clusters that contain at least one metal.

BACKGROUND

Mass spectrometry has developed into a useful tool to the biomedical community. Mass spectrometers used in biological applications primarily utilize either electrospray ionization (ESI), or matrix assisted laser desorption/ionization (MALDI), for transferring the molecules into a vacuum chamber. The mass analysis is typically accomplished using electrostatic or magnetic methods, or by time-of-flight (TOF) analysis.

Differences between the techniques arise from the methods used to generate the molecules in their ionic form. In ESI, the material is transferred to the high vacuum chamber while maintaining the ionic form that prevails in solution. In MALDI the laser desorption of the underlying matrix transfers molecules to the vacuum in either their neutral or ionic form. It has been estimated that only one out of $10^4$ molecules enter the vacuum as ions. Nevertheless, because the ion detector is extremely sensitive, the small fraction of molecules that do enter the vacuum as ions are easily detected and measured.

It is known in the art that photoionization techniques exist wherein lasers are employed simply to ionize the materials. While those techniques may operate satisfactorily for some applications, and have been exploited for commercial instruments, they are infrequently used by the biological community because they lack a convincing inherent advantage. A need thus exists to provide significant new information that cannot be obtained by other ionization schemes.

A need also exists to provide researchers with an inexpensive and rapid indication of the three dimensional shape of molecules and clusters of molecules.

As an example, the analysis of proteins by two dimensional (2D) gel electrophoresis coupled to mass spectrometry is insensitive to equivalent modifications of a protein that can occur at several sites. For example, stathmin, a tubulin binding protein, has several sites of phosphorylation. While isoelectric focusing and mass spectrometry can separate the non-, mono-, di-, tri-, and tetra-phosphorylated forms, neither method can differentiate forms of the protein that are monophosphorylated, but at different sites.

Further by example, the formation of correct disulfides in proteins are often required for proper function and protease resistance. Proteins with several cysteines in the amino acid sequence can have multiple forms due to cross-linking of the disulfides. The formation of incorrect disulfides can result in changes in the tertiary structure with consequent loss of enzymatic activity, or can result in changes in protein-protein binding. Unless the formation of non-native disulfides causes gross structural changes these alternative forms are not readily separable. It would be useful, therefore, to have available a shape-sensitive mass spectrometry technique that could readily resolve and quantitate the different protein forms due to alternative disulfide formation, or modification at each of a number of different sites.

In addition to the large molecules such as proteins, molecular clusters are an important cornerstone of nanoscale science. This importance derives from both their intrinsic interest, as well as their role as precursors in the production of cluster-assembled materials. Examples of clusters include atomically pure clusters such as those of carbon, which have achieved significant attention due in large part to an important member of the group, buckminsterfullerene. In addition there are clusters composed of metal atoms, rare gas atoms and metal oxides. In addition, there are composite clusters consisting of molecules with other molecules, and many combinations of rare gas or metal atoms are known.

Of particular interest to this invention are metallic clusters, composed of up to 40 atoms of transition metals such as nickel, palladium, or platinum. Such metallic clusters exhibit interesting structural and photophysical properties and, in addition, are important catalysts in many chemical reactions.

It is important to note that even relatively simple clusters exhibit a large number of stable isomers. Model studies suggest, for example, that the number of stable isomers grows exponentially with cluster size, reaching on the order of $10^{21}$ stable isomers for 55 atom Lennard-Jones systems. While not all of the theoretically calculated cluster isomers are necessarily present in a typical cluster source, studies have shown that even for small cluster numbers several isomeric forms have significant likelihood of being present.

Prior to this invention, however, there has not existed suitable instrumentation for identifying and segregating the different isomeric cluster forms. While mass selection of clusters is routine, the separation of isomers having the same or approximately the same mass, and the further identification and separation of clusters exhibiting isomer-specific properties, has not been accomplished in a satisfactory manner.

The importance of this need is significant. For example, both theoretical investigations and experiments have shown the catalytic function of a cluster to depend strongly on the number of atoms in the cluster. For example, in one study of the catalytic effectiveness of palladium clusters in the polymerization of acetylene, it was found that $Pd_6$ clusters produce the highest selectivity for generating butadiene, whereas butene is formed with the highest selectivity by the $Pd_{20}$ clusters. It is thus apparent that the structure of the cluster is closely correlated to its catalytic activity: certain cluster sizes have specific structures with certain exposed faces and steps. Given the large number of isomeric cluster forms that are possible, even for modest atom numbers, it is clear that the measured selectivities are averages over all cluster shapes in the sample. This suggests that the selectivity of the catalytic processes could be greatly enhanced if, in addition to the cluster mass, one were able to isolate specific cluster forms. Moreover, the possibility of assembling metastable species to form extended systems with novel physical or chemical properties makes the study of higher-energy cluster conformers of significance to the broader nanoscience community.

A typical cluster source generates a wide distribution of cluster masses and cluster structures. While it is straightforward to use mass spectrometric techniques to separate cluster masses, no technique existed, prior to this invention, to select specific cluster structures. In order to separate specific cluster shapes out of a mixture containing a large number of sizes and isomers, what is needed is an ability to exploit a property that allows the identification of one isomer vis-à-vis all the other isomers.

SUMMARY OF THE PREFERRED EMBODIMENTS

The foregoing and other problems are overcome, and other advantages are realized, in accordance with the presently preferred embodiments of these teachings.

This invention provides a method and an apparatus that operate based on a shape-sensitive photoionization technique. More specifically, this invention exploits Rydberg states for the purpose of performing shape-sensitive mass spectrometry.

The use of this invention provides an ability to add the dimension of molecular shape to mass spectrometry measurements. In a preferred embodiment this is accomplished by incorporating an ionization mechanism into a mass spectrometer instrument that is sensitive to the primary, secondary and tertiary structure of biologically important molecules such as proteins. The improved mass spectrometer instrument has a multi-dimensional output, where one dimension is the mass of a molecule, and where other dimensions are indicative of the three dimensional (3D) shape of the molecule.

This invention exploits the spectral properties of molecules, such as proteins, as well as molecular clusters, such as metallic clusters, for the purpose of providing a two-dimensional image that characterizes, or serves as a "fingerprint" for, the 3D shape of the molecule or molecular cluster.

An aspect of this invention is an instrument capable of providing shape-sensitivity to a mass spectrometer. The shape-sensitivity arises from a photoionization technique via one or more Rydberg levels. The energies of the Rydberg levels are shown to depend on the molecular structure, and can therefore be used to provide a fingerprint of the shape of molecules, such as proteins. Exemplary applications of the instrument include the analysis of protein shapes for the purpose of proteomics, and the diagnosis of disease states.

A further aspect of this invention is to provide an instrument suitable for the preparation, characterization, and manipulation of both minimum and higher-energy conformers of metallic clusters.

In accordance with a further aspect of this invention there is provided a method and an instrument for enabling the separation and isolation of specific isomeric cluster forms, thereby facilitating, as examples, a determination of isomer-specific properties, such as far-UV spectra, photoelectron spectra and ionization energies; the correlation of spectral properties to shape and structures of the isomeric forms; a determination of decay and interconversion dynamics of isomeric cluster forms; the injection of the cluster isomers into bulk gases; and a determination of the catalytic activity of isolated and isomerically selected clusters.

An aspect of this invention provides embodiments of a method and an apparatus to characterize a shape of an isomeric form of a sample comprised of a molecule or a cluster of molecules. The method includes raising an electron of the sample to a Rydberg state having an orbital diameter sufficient to encompass at least a portion of the sample; further raising the electron to an ionization state; and correlating the energy required to transition from the Rydberg state to the ionization state with the three dimensional structure of the sample. In a preferred embodiment raising the electron to the Rydberg state includes raising the electron to a first Rydberg state $Ry_1$, and then raising the electron to a second Rydberg state $Ry_2$. The operation of further raising the electron to the ionization state includes raising the electron from the $Ry_2$ state to the ionization state using optical excitation. The correlation operation preferably considers at least a wavelength of the optical excitation.

Another aspect of this invention provides embodiments of a method and an apparatus that use the Rydberg states to separate at least one isomeric form of a sample from other isomeric forms of the sample, where the sample is comprised of a molecule or a cluster of molecules.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein:

FIGS. 16A–G illustrate various expressions referred to in the specification.

DETAILED DESCRIPTION OF THE PREFERRED EMBODIMENTS

As is well known in the prior art, Rydberg states are highly excited electronic states of molecules that are related to the excited states of the hydrogen atom. Ionization of a molecule involves the ejection of an electron. If the electron is far away from a molecule, then it predominantly "sees" a positive charge. The Coulomb attraction between the electron and the positive charge gives rise to bound electronic states. As in atoms, states can be labeled with a principal quantum number n, and there are states that resemble s-orbitals, p-orbitals, or higher orbitals. In a large molecule, or in a cluster of molecules or atoms, the actual shape of the orbitals is dramatically different from those found in an atom. Nevertheless, since those labels refer to basic physical properties, such as radial and angular momentum, they may be used to categorize the Rydberg orbitals.

Figure 12:
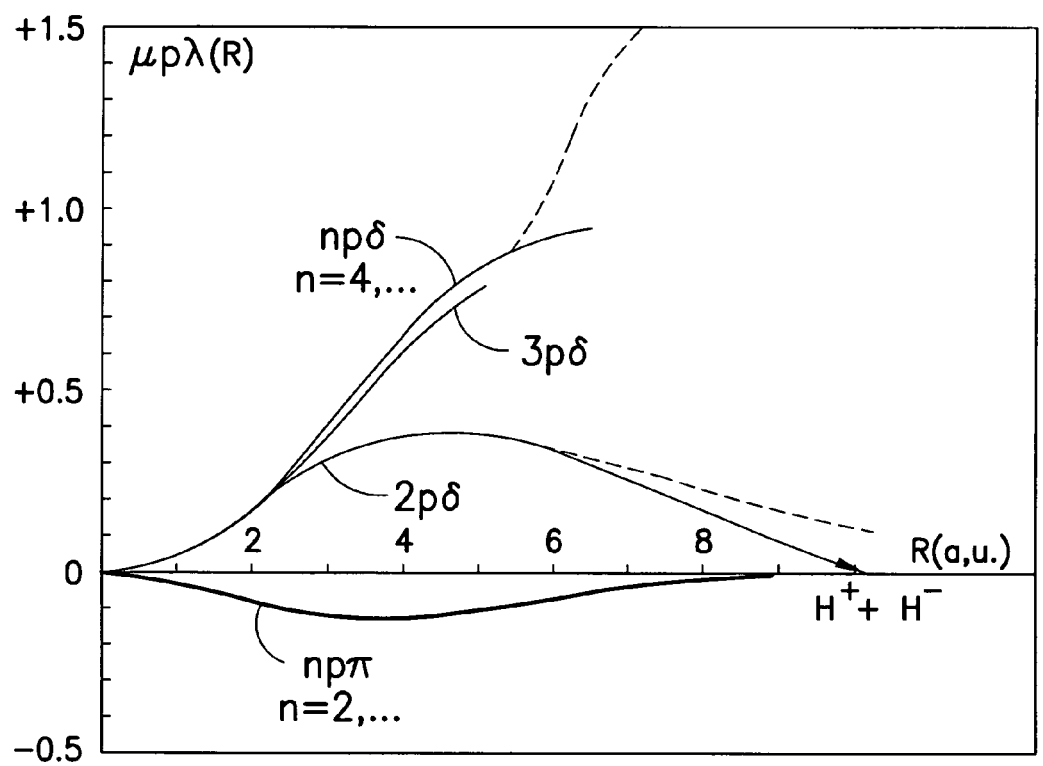
FIG. 12 shows the dependence of the quantum defect on the internuclear separation, in the case of the hydrogen molecule.

FIG. 12 illustrates the dependence of quantum defects for molecular hydrogen on the internuclear distance and on the angular momentum of the Rydberg electron, and shows that the quantum defects for such low-lying states: (1) are appreciable, (2) vary with structure (internuclear distance), and (3) depend on the angular momentum of the Rydberg electron. It can be seen in FIG. 12, for example, that the quantum defects for $H_2$ vary non-trivially with internuclear distance. Moreover, since the degree to which the Rydberg electron penetrates the molecular core depends on the angular momentum of the state, it can be seen that the quantum defects exhibit a strong dependence on the angular momentum of the Rydberg electron.

Figure 1:
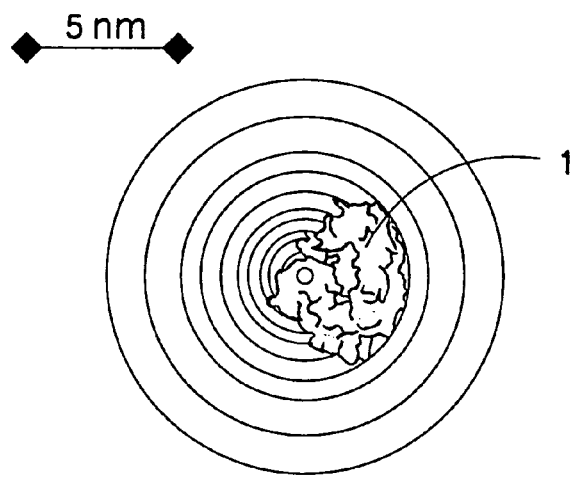
FIG. 1 shows a myoglobin protein, superimposed on an image of the wave function of the n=8, s-Rydberg state. The protein and the wave function are drawn to scale.

Of particular significance to this invention, it can be shown that an electron in a Rydberg orbital can have a very large size. For example, if the electron is in a state with a principal quantum number n=8, the orbit has a mean diameter on the order of 10 nm. This situation is illustrated in FIG. 1, which shows a hydrogenic s-type orbital superimposed on the scaled image of, as an example, a myoglobin protein molecule 1. The electron has a quantum mechanical wave function that is delocalized over a large volume which, in this case, encompasses all of the protein molecule 1.

As will be explained in detail below, the energy of the Rydberg state depends on the type and position of atoms and functional groups that reside inside the volume covered by the electron wave function. Measurement of the energy spectrum therefore, in accordance with this invention, provides a measure for the overall "shape" of the protein molecule 1. The shape in this context encompasses the physical shape, as well as the specific arrangement of functional groups that reside within the electron orbit.

It should be noted that the Rydberg electron orbital need not encompass the entire molecule or cluster of molecules, as the shape of that portion that is encompassed by the Rydberg electron orbital may still be characterized in accordance with an aspect of this invention. Alternatively, the molecule or cluster of molecules may be smaller than the Rydberg electron orbital such that it is completely encompassed by the Rydberg electron orbital.

It should further be noted that this approach contrasts significantly with other types of spectroscopy. IR spectroscopy, for example, provides a sensitive measure of very local regions of a molecule. The frequency of a C=O stretch vibration is determined by the force constant of the carbon-oxygen bond, which is only slightly affected by the immediate surroundings of the carbonyl group. In contrast, the Rydberg states are delocalized over very large volumes, and the energies of these states are therefore sensitive to global aspects of the molecular structure. The data derived from the measured energies of the Rydberg states may then be considered to provide a "fingerprint" of the global, large scale shape of the molecule of interest or, more succinctly, to provide a "Rydberg fingerprint".

In accordance with an aspect of this invention, the Rydberg states are used to provide a complement to other spectroscopies, as they are exploited to derive data that are indicative of molecular shape. Moreover, because the electrons in Rydberg orbits are already far removed from the ion core, a further aspect of this invention exploits these levels as steps on the path to ionization. One preferred, but non-limiting example of the synergy of the Rydberg state spectroscopy of this invention is with mass spectrometry. As will be described below, a novel apparatus and instrument measures two coordinates of the Rydberg fingerprint spectrum, and the mass of the molecule.

In a presently preferred embodiment for measuring large molecules, such as proteins, the MALDI approach is preferred for transferring the proteins into the vacuum apparatus of an instrument. However, instead of always measuring the flow of already-ionized particles, the instrument offers the flexibility to either examine positive ions, or to examine those molecules that enter as neutrals (non-ionized).

This invention exploits a photoionization path that depends sensitively on the shape and structure of a molecule. This method allows the instrument to output both the mass and the two-dimensional Rydberg fingerprint of the 3D shape of the molecule. This approach is thus fundamentally superior to previously used laser-based approaches discussed above.

Of some significance to the following description of the invention are the following points.

First, a protein can be ionized at many different locations. Each such ionization center gives rise to a specific spot in the fingerprint spectrum of Rydberg states. A protein with a specific shape will therefore typically be associated with many peaks in the Rydberg fingerprint spectrum (see, for example, FIG. 11). This fact further enhances the specificity of the Rydberg fingerprint. It is believed to be likely that the method preferentially ionizes certain amino acids, for example, tryptophan, phenyl-alanine and tyrosine. This selectivity serves to enhance the sequence specificity of the Rydberg fingerprint.

Second, it is believed that the shape of a protein within the vacuum apparatus is related to its shape in solution. This does not mean to imply that the shape needs to be identical, but rather that there is a direct correspondence between the solution phase shape and the shape in the vacuum. This point has received attention in the context of the connection between protein structure and the charge state distributions in electrospray ionization. It has been concluded that the protein shape does retain its identity in a mass spectrometer, and that mass spectrometry is a very useful tool to study protein structure and function.

Third, the presence of local charges in the protein molecule affects the energy levels of the Rydberg fingerprint, again increasing the specificity of the Rydberg fingerprint. As was noted above, this method operates both with neutral molecules and with positive ions. In either case, the removal of an electron increases the positive charge of the molecule by one.

Figure 2:
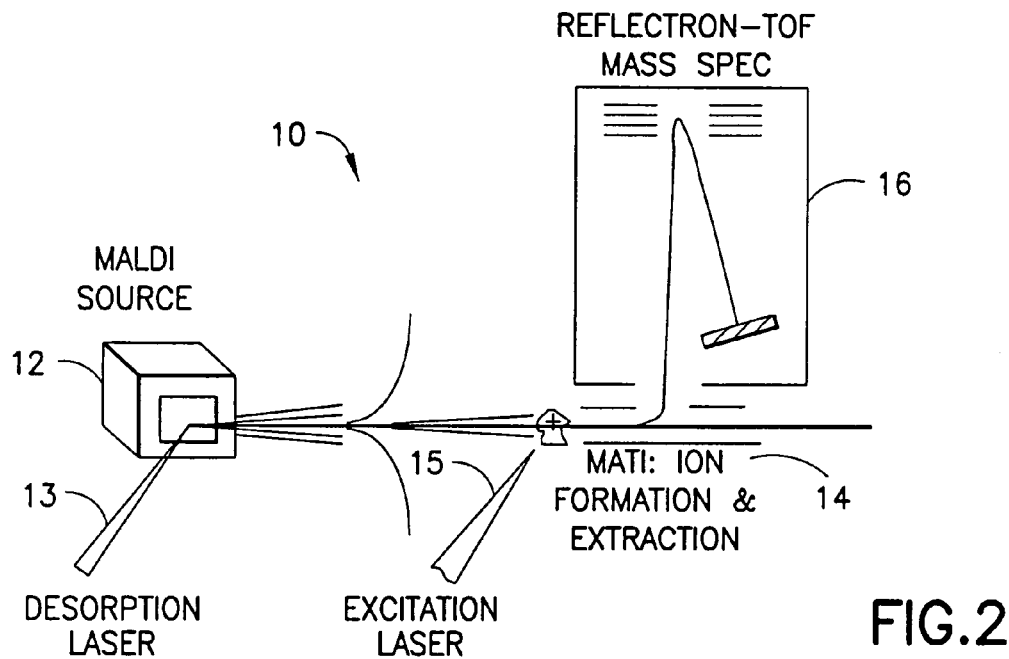
FIG. 2 is a block diagram of an instrument in accordance with this invention.

FIG. 2 shows an instrument 10 having three primary components, a MALDI (or ESI) region (MALDI source) 12, an ionization region 14, and a mass analysis region, such as a reflectron, time-of-flight (TOF) device 16. The MALDI source 12 operates with a beam 13 from a desorption laser (not shown), while the ionization region 14 operates with a beam 15 from an excitation laser (not shown). Of most importance to this discussion is the ionization region 14, where the shape-sensitive photoionization occurs. The MALDI source 12 and the time-of-flight mass analysis system 16 may be, in this embodiment, commercially available components.

The exemplary ionization scheme shown in FIG. 16A has been found to be suitable for use in accessing the Rydberg states. The excitation to the first Rydberg state, $Ry_1$, via the S2 electronic states, embodies several advantages. For example, the absorptions of several amino acids are strong at wavelengths of around 210 nm. Because the lifetime of the S2 resonance is short, the absorption bandwidth is large thereby enabling one to readily match the laser wavelength to the transition frequency of, for example, the amino acids tryptophan, phenylalanine and tyrosine. The short lifetime of the S2 states poses no problem, as it is preferred to use a short-pulsed laser for this step.

Figure 3:
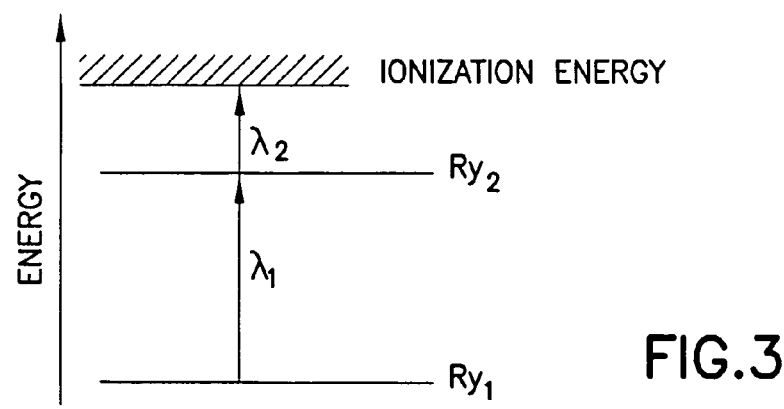
FIG. 3 shows a two-photon ionization from a Rydberg level $Ry_1$ via a second Rydberg level $Ry_2$.

In one embodiment the shape selective component of the ionization is the two-step excitation from $Ry_1$ to $Ry_2$, and then to the ion in its ground state, as shown in FIG. 16B and illustrated in FIG. 3. It should be noted, however, that in other embodiments one may transition through a single Rydberg level or state (e.g., $Ry_1$) before transitioning to the ionization state. Wile transitioning through a single Rydberg state may be suitable for some applications, transitioning through at least two Rydberg states (e.g., through both $Ry_1$ and $Ry_2$) is preferred, as it has been found to enhance the sensitivity of the instrument 10.

By selecting the ionization via the second Rydberg level, $Ry_2$, one obtains two quantum defect values, $\delta 1$ and $\delta 2$, corresponding to the Rydberg levels $Ry_1$ and $Ry_2$, respectively. Rydberg levels can be chosen such that the quantum defects are independent of each other. Therefore, each ionization center of a protein is characterized by a point in the plane spanned by two quantum defect coordinates. Each protein can have many ionization centers, so that the full fingerprint of the protein can be a large number of points in this plane.

The ionization is performed in such a way that only proteins that eject electrons at the threshold to ionization are detected. The technique, called Mass Analyzed Threshold Ionization (MATI) is well established, and is specifically designed to allow mass analysis in conjunction with photoionization.

In the presently preferred, but non-limiting embodiment of this invention, the shape sensitive photoionization process involves the spectral measurement of the transitions between two Rydberg states, and the transition to the ion. While in principle it would be possible to scan the laser wavelengths to obtain the two dimensional signature of the protein shape, this may not be a practical approach for an end-user instrument. Instead, it is preferred that the instrument 10 simultaneously uses a range of wavelengths, and then decode the wavelengths where the ionization occurs by a position of an event on an imaging detector.

Figure 4:
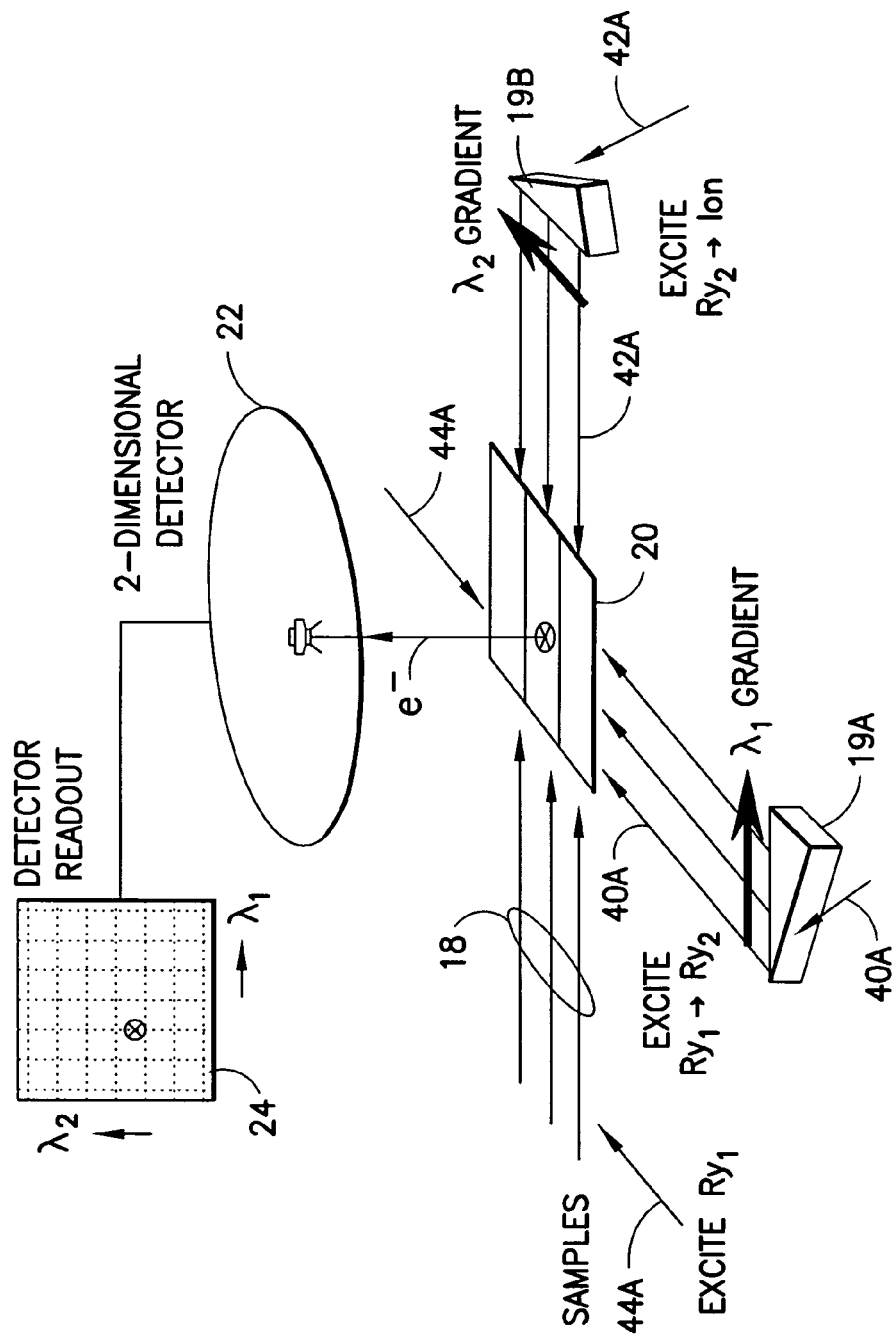
FIG. 4 shows a component of the instrument of FIG. 2 for decoding ionization wavelengths into a position on a two-dimensional detector.

This approach is illustrated in FIG. 4. A sample stream 18 enters the optical excitation region. The sample stream 18 could contain, as examples, molecules, such as protein molecules, or molecular clusters, such as metallic clusters. By spectrally dispersing, such as with prisms 19A and 19B, two broadband (e.g., two femtosecond) pulsed laser beams 40A and 42A (see FIG. 5A) in orthogonal directions, a two-dimensional gradient 20 of the laser wavelengths is established. The position where the incoming sample is ionized by the beam 42A is measured by accelerating the liberated photoelectron toward a position sensitive detector 22. The position readout 24 therefore provides a measure of the ionization wavelength(s) that the particular sample used during the ionization process, as a location on the detector 22 can be spatially correlated with a wavelength in the two-dimensional gradient 20.

It should be noted that the laser pulses 40A and 42A need not both be present at the same time within the two-dimensional wavelength gradient region 20, but may be time sequenced. In either case, for this two Rydberg level embodiment the beam 40A raises the electron from the $Ry_1$ level to the $Ry_2$ level, and the beam 42A raises the electron from the $Ry_2$ level to the ionization level.

Figure 11:
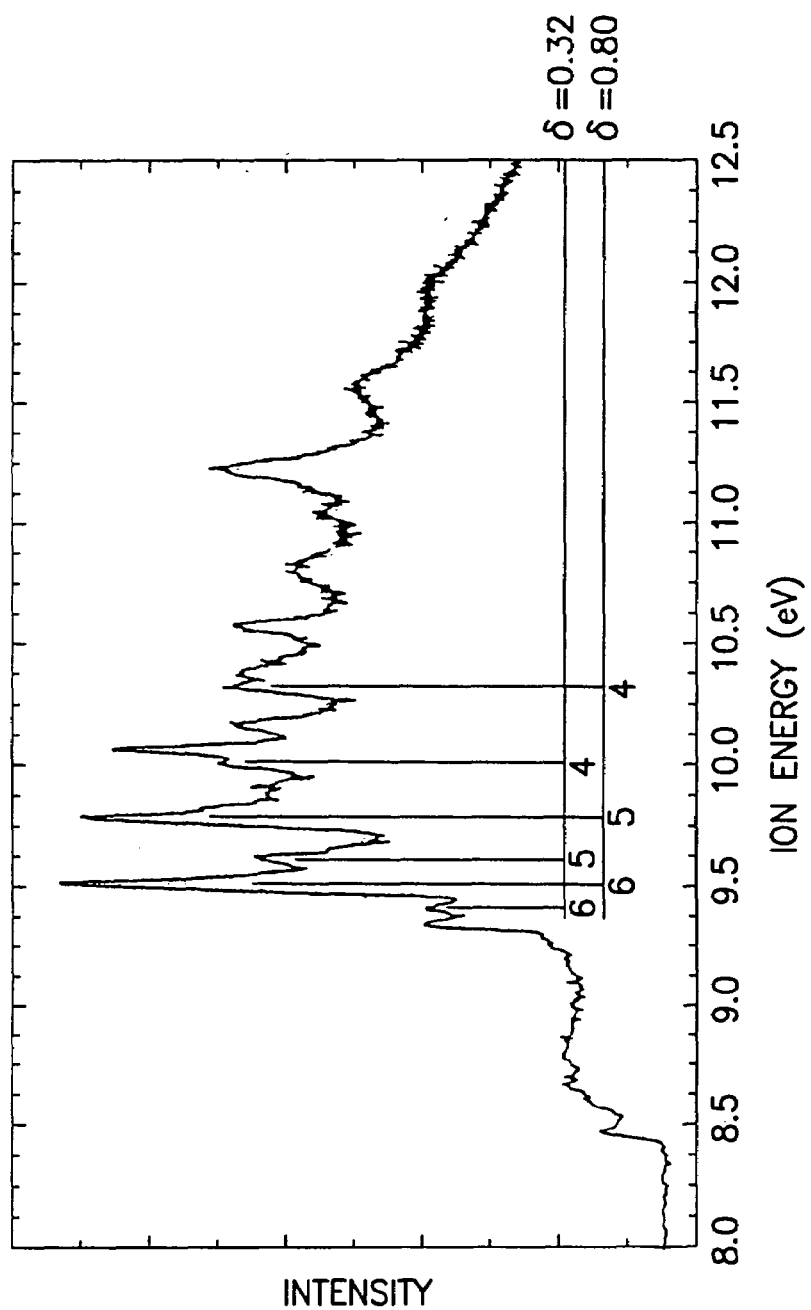
FIG. 11 shows the spectrum of observed Rydberg states during the photoionization of phenol, the volatile chromophore of tyrosine. Some transitions for n=6, 5 and 4 are indicated.

When using very short duration laser pulses, such as those in the femtosecond regime, the pulses maybe inherently broad band (e.g., 10–15 nm), and thus the prisms 19A, 19B are enabled to provide a continuum of optical energy over a wavelength band. Whether the beams 40A and 42A are present simultaneously or sequentially, the nature and extent of the spectral distribution within the two-dimensional wavelength gradient region 20 is assumed to be characterized and known a priori, thereby enabling a correlation to be made between the pixel location on the area detector 22 and a point (wavelength) within the two-dimensional wavelength gradient region 20 from whence the photoelectron originated. FIG. 11 shows the output of the detector readout circuitry 24, for one wavelength (i.e., location on the two dimensional detector array 20), which is essentially a count (intensity) of arriving photoelectron events plotted against a range of ion energies, where the ion energy is given by a subtracting the energy of the liberated photoelectron from the summation of the energies of the photons.

It is noted that the graph of FIG. 11 actually shows the result of the use of the Rydberg super-excited state (many Rydberg states present at once). The graph of FIG. 6, which plots the two quantum defect values $\delta 1$ and $\delta 2$, that correspond to the Rydberg levels $Ry_1$ and $Ry_2$, respectively, shows an example of the output data that is obtainable from the detector readout circuitry 24 for the case where only the Rydberg levels $Ry_1$ and $Ry_2$ are excited.

Figure 5A:
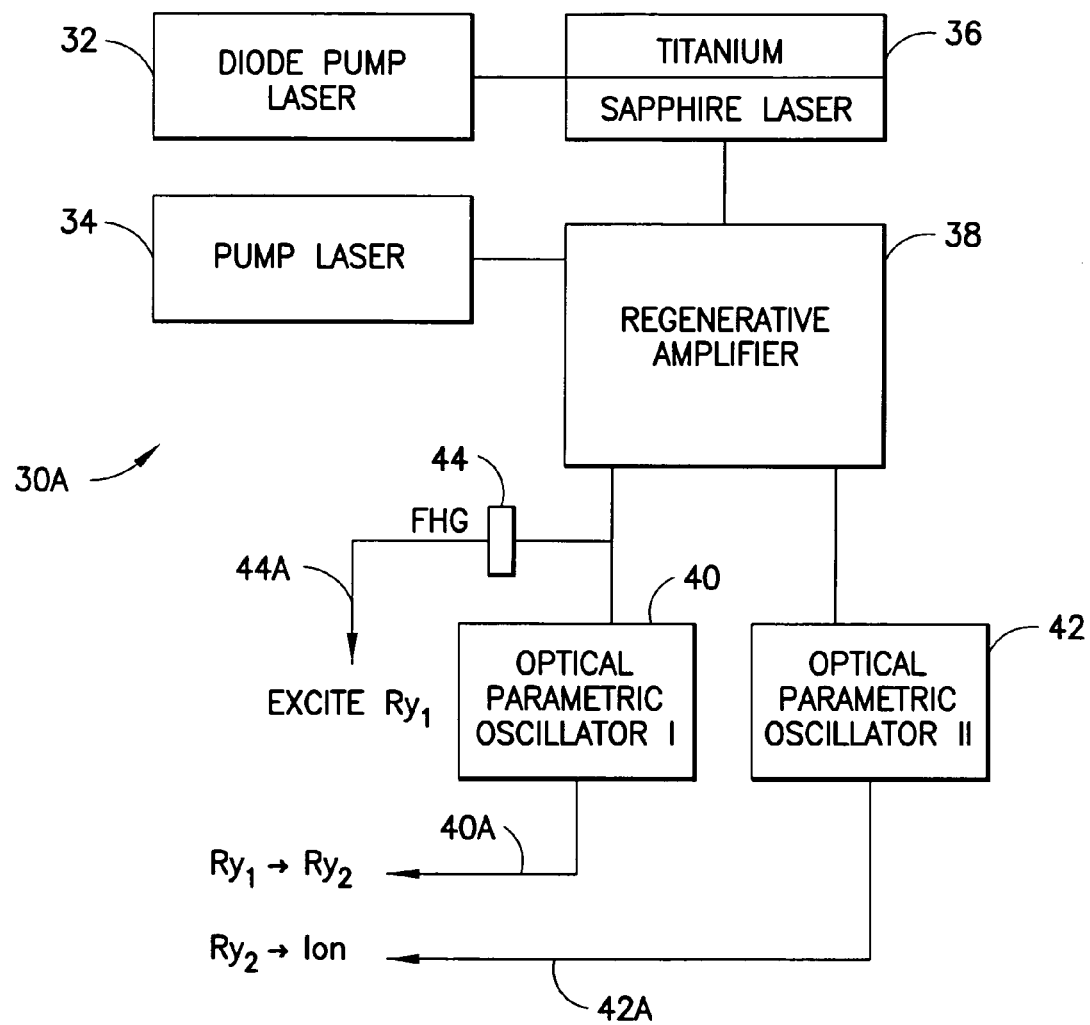
FIG. 5A shows the layout of a first embodiment of a laser system used for the structurally sensitive ionization.
Figure 5B:
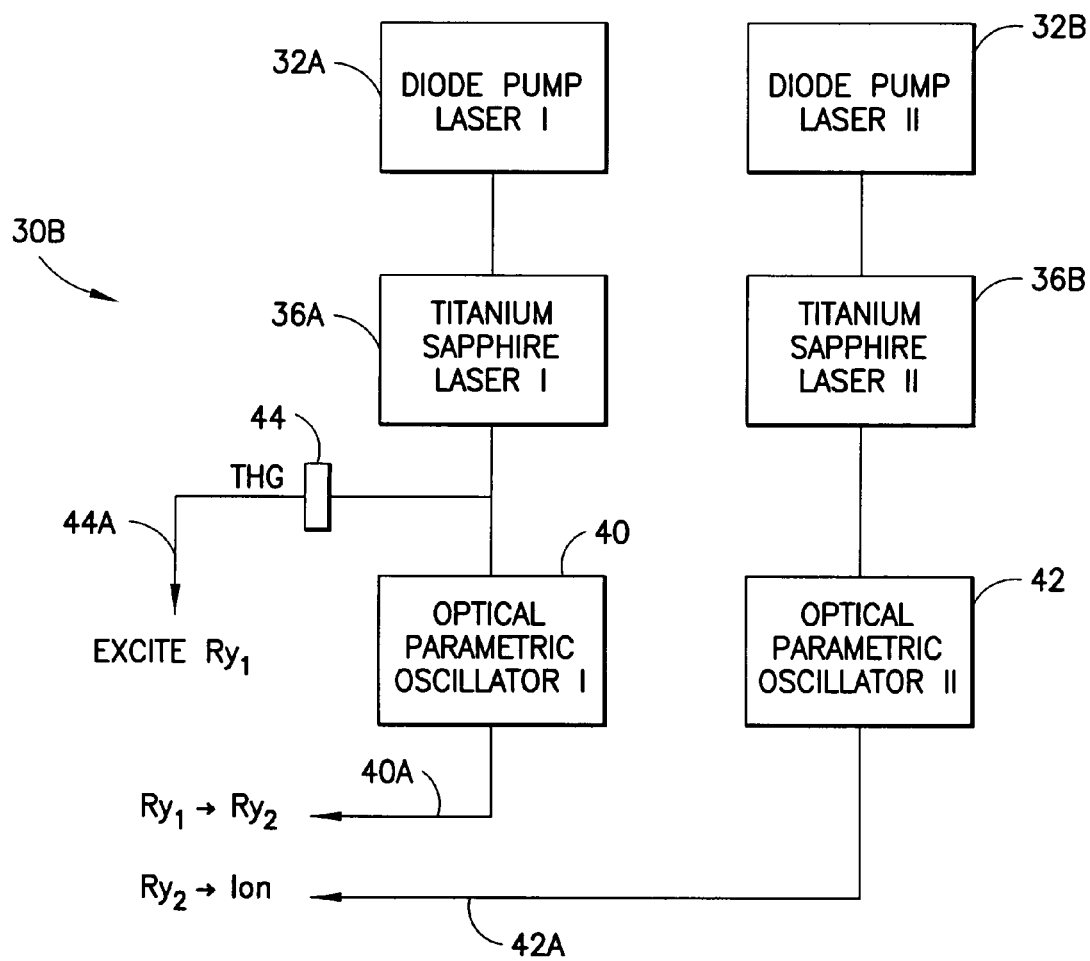
FIG. 5B shows the layout of a second embodiment of a laser system used to perform the structurally sensitive ionization.

It should be further noted that excitation 44A used to excite an electron from the valence band to the $Ry_1$ state (such as an electron beam or a UV source provided by a third or fourth harmonic generator 44 shown in FIGS. 5A and 5B), may be applied to the sample stream 18, or to the two-dimensional wavelength gradient region 20, both of which embodiments are also shown in FIG. 4.

It is important to keep in mind that in some applications this type of flexibility is not required, and thus the laser light sources used in FIG. 4, and the use of the wavelength gradient 20 and 2D detector 22, may be more complex than needed. In general, the embodiment shown in FIG. 4 enables one to explore which wavelength ranges are best suited for typical protein systems, or may be used where the nature of the input proteins is unknown. However, commercial instruments, such as those designed to detect the presence of one or a few specific protein molecules, may use relatively inexpensive laser diodes as sources, and simpler photoelectron detector arrangements.

Embodiments of laser systems 30A and 30B that are suitable for use in practicing this invention are shown in FIGS. 5A and 5B. In the embodiment of FIG. 5A the laser system 30A generates pulses using a diode pump laser 32 and a pump laser 34. The diode pump laser excites a titanium sapphire laser 36 and the pump laser 34 excites a regenerative amplifier 38. Two optical parametric oscillators (OPOs) 40 and 42 generate two independently tunable infrared laser beam outputs 40A and 42A, respectively, as needed for the transitions from $Ry_1$ to $Ry_2$, and from $Ry_2$ to the ion, respectively. In addition, the fourth harmonic of the laser beam (FHG), in the near UV spectral range, is generated by a FHG generator 44 and serves to excite the $Ry_1$ state in the proteins.

The alternate embodiment of the laser system 30B shown in FIG. 5B employs dual Titanium-Sapphire lasers 36A, 36B each pumped by a diode pump laser, 32A, 32B, respectively, to produce pulses with 2 picosecond duration and a repetition rate of 80 MHz. One part of this laser output is used to prepare and excite the sample, such as the metallic clusters discussed below, via in this case a Third Harmonic Generator (THG) 44, while the remainder is used to pump the two synchronized optical parametric oscillators (OPOs) 42 and 44, thus generating the two infrared laser beams 40A and 42A.

As was discussed above, the infrared laser beams 40A and 42A are spectrally dispersed to generate the 2-dimensional wavelength gradient 20 shown in FIG. 4. The position at which a photoelectron is detected provides the two dimensional fingerprint. Clearly, since a protein can have many different ion cores, a protein will be characterized by many points on the detector 22. In order to ensure that each protein molecule is ionized only at one center, the laser intensity is preferably kept below some threshold intensity at which ionization will occur at more than one center. The image on the detector 22 is formed by repetitive ionization of many protein molecules in the beam. The ions themselves may be subsequently accelerated to the reflectron time-of-flight instrument 16 shown in FIG. 2. One suitable type of reflectron TOF instruments is available from Bruker Daltonics, Inc.

By this technique the detection of the photoelectrons enables the Rydberg fingerprint to be derived, thereby enabling the sample shape to be characterized, while the sample ion mass can be almost simultaneously measured by a mass spectrometer instrument. Alternatively, this technique allows a sample ion to be separately collected on a substrate or in a vacuum or other region, enabling the separation and segregation of a desired isomer of the sample ions based on a desired Rydberg fingerprint (sample shape). In this latter case the arrival of a photoelectron at a predetermined detector 22 pixel location is indicative of the presence of an ion of the desired isomer, which can then be used to trigger an electrostatic deflection of the ion to the collection region.

An exemplary specification of the parameters of the laser system 30A of FIG. 5A is as follows: pulse duration 100 fs, wavelengths 300–3000 nm, pulse repetition rate 1 kHz and output pulse energy 0.1 mJ. It is noted that commercial laser systems are available that cover a wide range of these parameters.

In the preferred embodiment the two dimensional detector 22 is based on an imaging microchannel plate coupled with a resistive anode divider. One suitable detector device is available from Quantar (a division of Kore Technology, LTD). In other non-limiting embodiments the detector 22 could be based on, for example, a CCD coupled with a phosphor coating for generating detectable light in response to an impinging photoelectron. The output signal of the detector 22 is preferably digitized and stored on a PC (not shown) equipped with a multi-dimensional, multi-channel analyzer, such as one available from Comtech.

Figure 6:
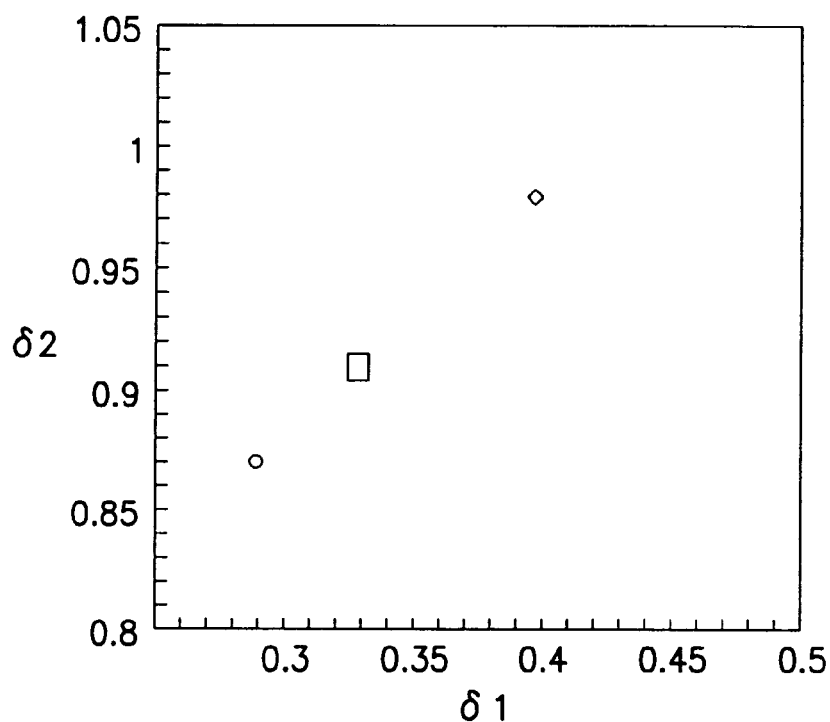
FIG. 6 shows in a simulated space the quantum defect values $\delta_1$ and $\delta_2$ for the case of pyrazine (◇), pyrazine-Ar (+) and pyrazine-Xe (o).

The instrument 10 may output a signal as a function of three dimensions. One axis is the conventional mass spectrum output, while two axes represent the two values of the quantum defect of the protein molecule 1 (see FIG. 6). As an illustration of the two dimensional output, one may take the numerical example of rare gas atoms, bonded through-space to an aromatic ring. FIG. 6 shows a contour plot of the positions of the different clusters in the plane spanned by the two quantum defects $\delta 1$ and $\delta 2$. For this plot, the spectral resolution is assumed to be 10 $cm^{-1}$, a value that is consistent with a 1 ps lifetime. The intensity is indicated (logarithmically) as simulated by a Gaussian signal with a width in the $\delta$ space of 0.002, as appropriate for ionization from n=4. The space shown in FIG. 6 is representative of the range over which typical quantum defects of s- and p-angular momentum states vary, or about 0.3 $\delta$ units. Dividing this space by the size of the resolution element, one determines that there are 150 resolution elements in each dimension spanned by the quantum defects. The two-dimensional space available to map the shapes of proteins, as well as the cluster isomers discussed below, is therefore on the order of $150^2=22,500$ pixels. This space is further enhanced by the presence of many points for a single protein shape. In general, all points must agree for two structures to be declared identical. For this reason, the dimensionality of the shape fingerprint calculated above is to be considered conservative.

The flexibility inherent in the instrument 10 enables one to determine which Rydberg states are best suited for the shape-sensitive photoionization technique. As the principal quantum number n is increased, the diameter of the Rydberg orbit increases with $n^2$, the ionization energy of the level decreases as $n^2$, and the lifetime increases as $n^3$. If n is small the lifetime is most likely too short to be useful. However, as the value of n increases, the lifetime increases as the third order, while the diameter increases as the second power of n. At n equal to 4 or higher, one enters a range where the lifetime is long (typically >100 ps), and the structural sensitivity is high.

At higher values of n, the electron will eventually be in such a wide orbit that it may loose its sensitivity for the protein molecule structure. However, the resolution of the instrument 10 has been found to increase as well for the larger Rydberg orbital diameters. The diameter of a Rydberg orbit with n=15 is about 36 nm. Since the sizes of typical proteins with masses between 5,000 and 500,000 au are about 2 to 10 nm, it is likely that n=15 is too large a value for many proteins of interest. Therefore, there exists a range of values of the principal quantum number n, in a range between about 3 and about 15, that may prove to be optimal for the fingerprinting of most, if not all, protein molecule structures, as well as for use in fingerprinting many types of molecular clusters. However, the use of this invention is not limited to any specific principal quantum number or range of principal quantum numbers. As one example, it may be found that excitation using a microwave source, as opposed to an optical source, can enable the use of principal quantum numbers of the order of 100. Thus, it should be appreciated that the teachings of this invention are not to be construed to be limited with regard to specific values or ranges of values of Rydberg principal quantum numbers.

In addition to the size of the Rydberg orbits, there are experimental factors that affect the utility of energy levels. Those factors include the output power of the laser system at the particular wavelength, the availability of good optical components, the possibility to focus the light to a small spot, and the cross sections for transitions between Rydberg levels. Considering all of these factors, it is difficult to a priori determine the most optimum quantum numbers.

The laser system 30 provides tunable radiation ranging from the near UV (300 nm) to the far IR, e.g., up to about 10 micrometers. Using the quantum defect formula, one can calculate that for a typical $\delta$ of 0.5 one can characterize Rydberg levels with quantum numbers from n=3 up to n=11. While this range falls short of the very highest conceivably useful quantum numbers, it does cover most of the range of interest.

Suitable light sources for causing the various transitions are as follows:

$S_1$ to $Ry_1$: nitrogen or YAG laser, excimer laser, solid-state far UV laser; and $Ry_1$ to $Ry_2$ and $Ry_2$ to ion: quantum cascade laser, laser diode.

The light sources used to excite the Rydberg states can be similar to, or identical to, those lasers that are used in conventional MALDI instruments. In fact, in one embodiment of this invention it is possible to use the same nitrogen or YAG laser for both the MALDI desorption and for the excitation to the Rydberg levels.

To induce the transition between the Rydberg levels, and the ionization from the Rydberg level, an IR laser is required. Either small laser diodes or quantum cascade lasers may be employed to advantage. Quantum cascade lasers are semiconductor devices that are more powerful than conventional diode lasers. Typical dimensions of the active structures are about 2 mm×1 mm×20 micrometers, and the entire device is packaged on a chip with dimensions of 1 inch or less. This laser can thus be mounted within the vacuum chamber, which beneficially avoids absorption of the IR output by atmospheric vapors. These lasers operate at specific wavelengths ranging from 3.4 micrometers to 17 micrometers. While the lasers can be temperature tuned over small ranges, they are typically engineered to operate at a specific wavelength of interest. However, broadband operation of quantum cascade lasers has been reported, which makes them suitable for use as the broadband laser.

As should be apparent, the shape sensitive mass detection made possible by this invention provides a tool that is useful for a wide variety of applications in the biomedical community. These applications encompass protein folding studies, the analysis of complex mixtures for proteomics, pharmaceutical development for diseases resulting from protein misfolding, and the confirmation of the consistency of tertiary structure under diverse conditions.

Discussing these now in greater detail, the characterization of protein folding has been recognized as an important facet of biochemistry. In recent years investigations of folding events have been stimulated by the recognition that a number of "conformational" diseases are a result of protein misfolding or aggregation. In addition to the direct connection to human disease, the detailed understanding of protein folding has bearing on the biotechnology community. The ability to heterologously express functional proteins is often limited by the rate of folding or the solubility of particular domains. Methods have been developed to aid soluble protein production by increasing folding rates, optimize amino acid sequence, alter host genetics or modify growth conditions. Existing procedures for assessing solubility and folding are tedious and make the screening of large numbers of genetic constructs or growth conditions impossible.

The shape sensitive detection in accordance with this invention can be used to probe the thermodynamics and kinetics of protein folding on time scales ranging from microseconds to days. Since only a small amount of sample is required, individual bacterial colonies can be rapidly assayed for correctly folded expression products. In addition, events that are transient in nature are accessible for study. Dynamic protein complexes, such as the conformational changes resulting from phosphorylation of methylesterase CheB, which last on the order of two seconds, can be readily observed.

This invention also has application to proteomics. The current standard for proteomics analysis is 2-dimensional electrophoresis (2DE). Recently the electrophoresis step has been coupled with mass spectrometry to aid in the identification of resolved proteins. The electrophoresis is a relatively time-consuming operation and is resistant to easy automation. In an attempt to accelerate throughput, mass spectral methods for the analysis and unambiguous identification of proteins from samples representative of an organism, cell or tissue type have been developed. However the use of only mass analysis limits the resolution of the technique and, as a result, other parameters must be constrained through, for example, the use of separations, enzymatic digestions, and post isolation labeling.

The development of a high-throughput method capable of analyzing complex mixtures provides a critically needed tool for the functional analysis of biological systems. In accordance with an aspect of this invention, an instrument exhibiting shape selective detection, coupled with mass spectrometry, provides a method to rapidly differentiate cell types, resolve different metabolic states of a particular cell type, and to distinguish therapeutic effects of individual proteins.

A number of disease states such as cystic fibrosis, and some forms of cancer, are a result of misfolded proteins. The formation of aggregates of misfolded proteins are implicated in Alzheimer's, scrapie, Huntington's and Parkinson's disease. Evidence indicates that the formation of early intermediates on the pathway to large aggregates or plaques is the cause of Alzheimer's and Parkinson's disease. The identification and quantification of misfolded peptides that may be the nucleus for the formation of early aggregates is an important target for understanding these diseases. However, prior to this invention there was no method available for the rapid and sensitive analysis of proteins based on shape and, as a result, pharmaceutical development in these areas has trailed advances in other areas.

The ability provided by this invention to rapidly assay samples for correctly folded proteins facilitates the efficient discovery of drugs that may promote the folding or inhibit the aggregation of these disease related proteins. It has been reported that small molecules are capable of stabilizing a folding mutant of p53 in a soluble and functional form, with resulting recovery of the protein's ability to inhibit tumor growth. Assays that currently exist for the detection of misfolding are relatively slow and are not suitable for high-throughput screening. The use of the instrument 10 described herein provides new avenues for understanding the molecular mechanisms of diseases resulting from misfolding events, and aids in the rational design of strategies to control protein misfolding.

This invention also finds utility in the characterization of protein structure. The 2-D fingerprint of a protein can be used to determine the fidelity of the tertiary structure of a protein in vitro. Assay of proteins and enzymes in vitro is premised on the notion that the in vitro structure and activity is indicative of behavior in vivo. Control reactions or binding events can be used as confirmatory events, but are limited to defining the characteristics of the specific site of interaction. If binding events of proteins or small molecules are being probed at alternative sites there is no guarantee that the controls are relevant. To determine if the in vitro milieu duplicates the in vivo environment, a more universal analysis is required.

While the 2-D Rydberg level shape fingerprint does not immediately yield a three-dimensional structure, each fingerprint can be associated with particular protein structures. Thus, the analysis of a protein ex vivo provides a spectrum that can be compared to the same protein in an in vitro assay, or following deposition on a solid substrate during fabrication of a protein array. The analysis is capable of verifying that the entire structure of the protein of interest is relevant, and serves as a unique method to verify experimental design.

In addition to the significance of this invention in the foregoing fields, applications exist as well in any field where oligomers and polymers, both of biological and technical nature, need to be analyzed for shape. This includes fields such as polymer science, where the instrument 10 may be used to analyze the shapes of polymeric compounds. Furthermore, the technique lends itself to time-resolved studies of molecular structures, and can therefore be of use in research on chemical reaction dynamics.

The shape-sensitive photoionization/mass spectrometry made possible by this invention provides distinct advantages over other, existing methodologies. As was discussed, a technique that has a benchmark status in the biomedical community is 2-dimensional electrophoresis, which can be coupled with conventional mass spectrometry. This invention provides specific advantages over conventional 2DE. First, the shape sensitive technique can be made an integral part of the mass spectrometer, and can therefore be readily automated and systematized. In contrast, automation of 2DE remains a unfulfilled goal. Second, the shape-sensitive photoionization/mass spectrometer of this invention is capable of performing an analysis much faster than is possible with 2DE, such as within about one minute. Third, the shape-sensitive photoionization/mass spectrometer of this invention provides a measure of variability inherent in the biomolecular structures, by measuring the widths of the spectral peaks. An ability to handle such variability is beyond the capability of conventional 2DE.

In addition, there exists the possibility to directly determine the shape of a protein from the spectral fingerprint, providing a useful complement to structural analysis by x-ray diffraction and nuclear magnetic resonance.

Another technique that is often used in the context of structural analysis of proteins is tandem mass spectrometry (MS/MS), where fragmentation between the two mass spectrometer components provides a measure for both the mass and the composition of a protein. The following points can be used to differentiate the shape-sensitive photoionization/mass spectrometer of this invention from MS/MS.

First, the shape-sensitive photoionization/mass spectrometer measurement provides a distinction based on the shape of a protein, whereas MS/MS is used to obtain sequence information by detecting fragments and fragmentation patterns. MS/MS is not sensitive to variations in the tertiary structure of a protein.

Second, the shape-sensitive photoionization/mass spectrometer measurement provides information regarding the similarity of different proteins. Proteins with unknown shape can be compared to proteins with known shapes, and qualitative information regarding shape similarity can be obtained.

Third, the shape-sensitive photoionization/mass spectrometer measurement can correlate the shapes of the same protein in different environments. For example, it may be possible to relate the crystal structure of a protein to its solution phase structure, or to determine if there is a difference between the shape of a protein in solution and on a solid surface of a microarray.

In addition, it should be noted that there are methods to study the charge distributions in protein ions, or use mass spectrometers in conjunction with deuterium exchange, to obtain information about the structure and function of proteins. While those techniques are quite useful, they are not nearly as structure-specific as the shape-sensitive photoionization/mass spectrometer measurement made possible by this invention.

Discussing now in greater detail the underlying physical mechanisms that are exploited by the shape-sensitive photoionization instrument of this invention, with or without the use of a mass spectrometer, it is noted that the Coulomb interaction between a negatively charged electron and a positively charged ion core always gives rise to an attractive potential that supports Rydberg states. While spectroscopists have not yet studied Rydberg states of proteins, their existence has been utilized in many studies on large molecules, as well as molecular cluster aggregates. Rydberg states have also been observed in condensed phases and spectra of molecular systems at high pressure. Specific experiments have shown that even a strongly electron scavenging neighboring molecule does not eliminate Rydberg states. Apparently, it seems, local charges do not override the fundamental necessity that there be bound states between a positive ion core and an electron. There is therefore little doubt that proteins support Rydberg states. The important point is that the energy of the Rydberg levels does indeed depend on the three dimensional structure or shape of the protein.

Electrons in Rydberg orbitals experience a potential that closely resembles that of a positively charged point source. The energy level structure, $E_n$, of Rydberg states is frequently described by the quantum defect formula shown in FIG. 16C, where IP is the ionization potential of a particle, $R_y$ is the Rydberg constant (109,736.6 $cm^{-1}$), and n is the principal quantum number. $\delta$ is the quantum defect, a parameter that is constant for any given molecule. From the formula it can be seen that the ionization energy of a level with integer quantum number n, that is, IP–$E_n$, is directly related to the value of the quantum defect. In this discussion the quantum defects are referred to as the observables. Values of $\delta$ typically range from 0 to 1.

Figure 7:
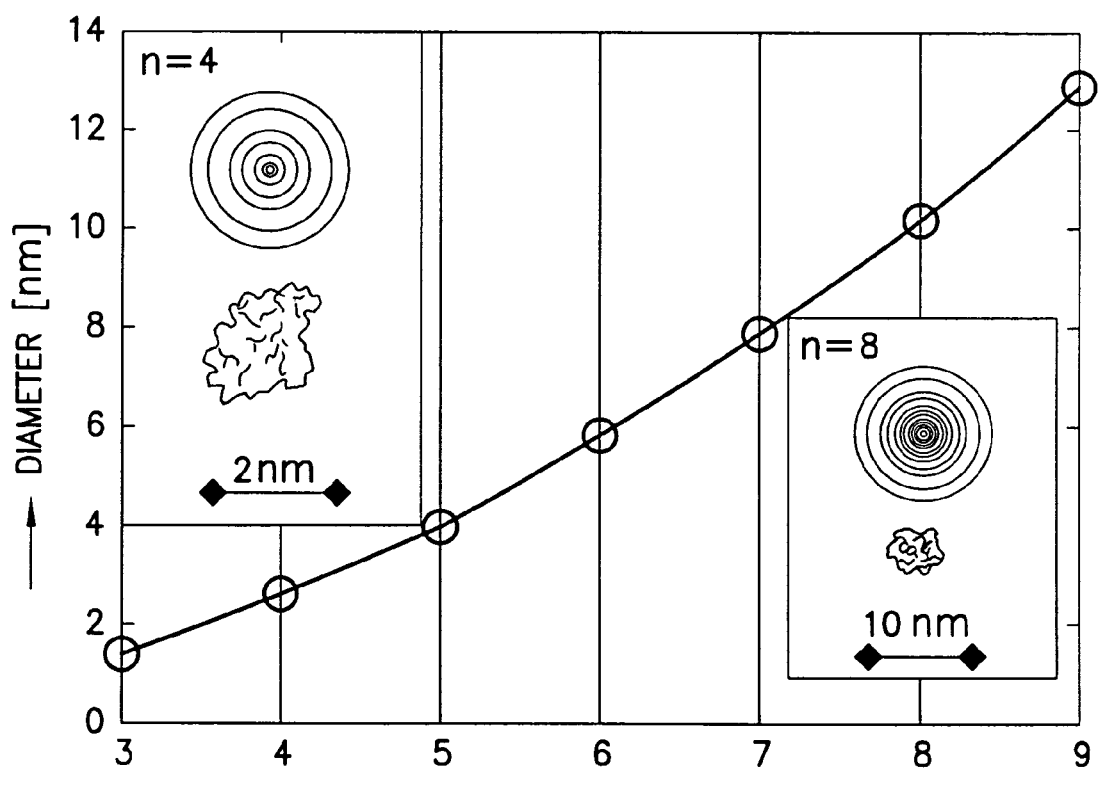
FIG. 7 shows the diameter of electron orbits as a function of principal quantum number n (s=0). Left inset: the n=4 orbital, and an insulin protein, drawn to scale. Right inset: the n=8 orbital and a hemoglobin protein.

Of significance to this discussion is the fact that an electron in a Rydberg orbital occupies a volume that is similar to, or larger than, all but the largest proteins. FIG. 7 depicts the diameter of the Rydberg electron as a function of the quantum number n. The principal quantum number can be optimized in the instrument 10 to give good results for a wide range of proteins, or it may be specifically selected for a protein or proteins of interest.

The quantum defect $\delta$ is sensitively dependent on the molecular system. The theoretical description of quantum defects is based on multichannel quantum defect theory (MQDT). While MQDT is complex, qualitatively there are two reasons why the $\delta$ values are molecule-specific. Both reasons support the contention that quantum defects are dependent on the structure of a protein.

Figure 8A:
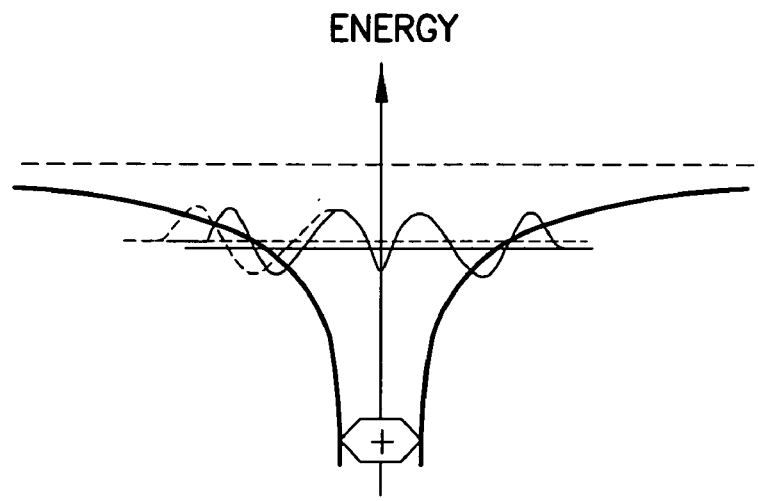
FIG. 8A shows that as the wave function (solid line) is scattered off the ion core it experiences a phase shift (dotted line). Destructive interference occurs unless the energy level adjusts.

The first reason is related to scattering, as shown in FIG. 8A. The electron in a Rydberg level orbits the ion core. After each round trip, the wave function of the electron must constructively interfere with the wave function of the previous orbit. As the electron passes through the ion core, it is scattered, which causes a phase shift. To accommodate this phase shift, the Rydberg state must adjust its energy to maintain constructive interference. Since the phase shift depends on the type and position of atoms and functional groups, the energy depends on the shape of the molecule.

Figure 8B:
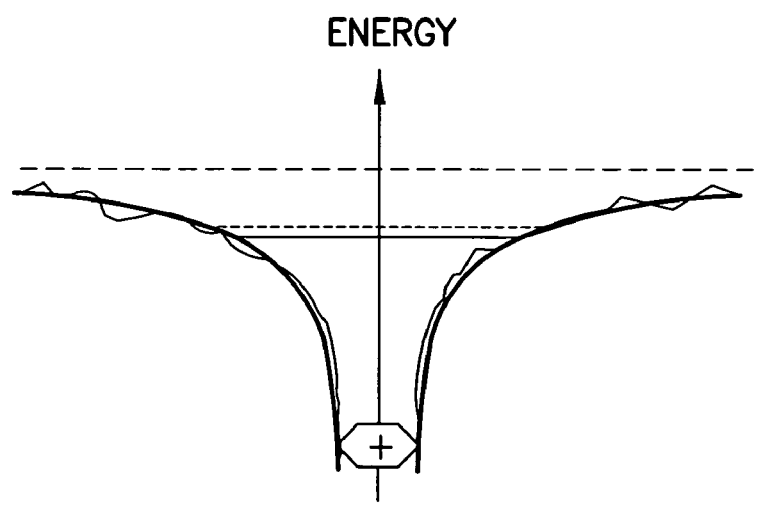
FIG. 8B shows the coulomb potential modulated by the presence of peripheral functional groups and, as a result, the energy level shifts.

The second reason is related to a corrugated potential view, as shown in FIG. 8B. This is an alternative approach for considering the Rydberg level system, by assuming that the potential between the ion core and the electron is modulated by the presence of other atoms, local negative and positive charges and dipole moments. In spite of the modulations of the potential by such perturbations, there are Rydberg-like energy levels, albeit at different energies. The exact energy of the Rydberg levels is again dependent on the spatial arrangement of functional groups inside the volume spanned by the Rydberg electron.

Figures 9, 10:
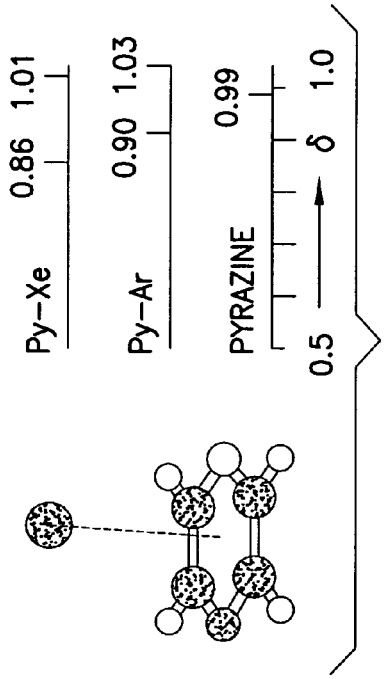
FIG. 9 is a Table that shows the quantum defects of certain structural isomers.
FIG. 10 shows the quantum defects of pyrazine, and through-space bonded complexes with rare gas atoms.

The qualitative aspects of the foregoing are confirmed for many molecules in which Rydberg states have been investigated. Table I, shown in FIG. 9, lists the quantum defects for two series of structural isomers of small aromatic molecules. This is a particularly challenging case, because in these molecules the only structural difference relates to the interchange of a nitrogen atom and a C—H group. As can be seen, the differences between the quantum defect values are on the order of 0.1. This value is much larger than the resolution of the instrument 10, which exhibits a resolution on the order of ±0.002, on the δ scale shown in FIG. 10. It is also noted that the dependence of the quantum defect on the structure of proteins should be even larger, since many more atoms affect the quantum defect value. The effect of protein structure on the shape fingerprints is therefore significantly more pronounced.

It is important to emphasize that the quantum defect is not an effect of a specific molecular bond, or a particular electronic structure of the molecule. This point can be illustrated by experiments reported by Fujii et al., "Vibrationally autoionizing Rydberg clusters: Spectroscopy and dynamics of pyrazine —Ar and —Xe clusters", J. Chem. Phys., 1134, 18, 8000–8008 (2000), who have examined the Rydberg spectra of pyrazine (1,4-$C_4N_2H_4$) complexed by a single rare gas atom (see FIG. 10). These authors reported that the quantum defect δ changes from about 0.09 upon complexation with argon, to about 0.13 for complexation with xenon. These changes in the quantum defect are again much larger than the resolution of the instrument 10, and are thus resolvable. Moreover, Fujii et al. observe that the breaking of the symmetry upon complexation leads to the observation of additional Rydberg levels that are not observed in the bare pyrazine molecule. Such symmetry related effects enhance the distinctiveness of the Rydberg fingerprint data that is obtained using the instrument 10.

In accordance with the foregoing the following two points are noted. First, the proximity of even a rare gas atom, which does not form any chemical bond to the molecule, significantly alters the quantum defect spectrum. Second, and even though argon and xenon are chemically very similar, the difference in the mass and the small difference in their separation from the aromatic ring have a pronounced effect on the spectrum.

Based on the foregoing examples, it can be further appreciated that the folding of proteins strongly affects the energies of the Rydberg levels, therefore providing the desired sensitivity to the protein shape.

There are many perturbations between different ionization channels, which tend to shift energy levels. The channels relate to different states of the final ion, which in a large molecule includes a large number of vibrations. However, it should be noted that the coupling between the Rydberg electron and the protein vibrations is very small. The interaction with a dense set of vibrational states gives rise to a single band that is broadened by the inter-channel couplings. In the time-domain, the broadening is observed as a decay of the Rydberg state. This decay depends on the principal quantum number, with larger quantum numbers giving rise to slower decay, on the grounds of a weaker coupling. This point is discussed in further detail below.

In a traditional threshold photoionization experiment one measures the ionization energy from the ground state. This quantity is greatly affected by thermal vibrational excitation of the molecules, leading to broad lines. In contrast, the observable of interest to this invention is the ionization energy out of a Rydberg state, $IP-E_n$. This value is not affected by thermal congestion, because the potential of the Rydberg state is largely independent of the vibration, as was described in the previous paragraph.

It is known that the charge created during an ionization event can migrate from an amino acid chromophore to neighboring sites. It should be further noted that the mechanism exploited by this invention is not affected by such charge migration, as the shape-sensitive part of the ionization is performed after the charge migration in the ion core is complete.

In summary, based on the foregoing discussion it can be seen that: Rydberg states of proteins exist, and even though their energies are difficult to calculate with current methods, they do offer a way to fingerprint the shape of proteins; the energies of Rydberg states are sensitively dependent on the type and spatial arrangements of those atoms and functional groups that are within the volume of the Rydberg electron, and this sensitivity is independent of the existence of chemical bonds; and Rydberg states offer great flexibility for shape sensitive ionization, as their size can be chosen by selecting different orbits. This inherent flexibility can be exploited to tune the instrument 10 to states that are most sensitive of protein shapes.

The use of the Rydberg levels in accordance with this invention can be broken down into two parts: accessing these states, and examining their spectroscopy. Absorption cross sections for transitions from the ground state of a molecule to a Rydberg state are often rather small. However, several pathways to Rydberg states have been discovered that involve highly excited valence states. A non-limiting example of how one can efficiently access Rydberg states is depicted in FIG. 16D.

In this example the molecule in its ground state ($S_0$) is excited to the Rydberg states ($R_y$) in a stepwise fashion via the valence electronic states $S_1$ and $S_n$. The highly excited $S_n$ state quickly relaxes into the set of Rydberg states. To probe the Rydberg states, photoionization is coupled with photoelectron spectroscopy. The scheme is depicted in FIG. 16E. The kinetic energy of the outgoing electron $e^-$ is measured and analyzed, as was described above with respect to FIGS. 2, 4 and 5. FIG. 11 shows a spectrum of phenol obtained in this fashion. As can be seen, while the ionization scheme may appear unusual and complex, the signal is in fact quite strong and easily observed. Many Rydberg transitions are seen, and a few series with constant δ and different quantum numbers n are labeled.

This invention can employ other ionization pathways as well. Among these is the excitation to the $S_2$ state as the first step, and the generation of the Rydberg states via superexcited molecular states (see, for example, "Ultrafast dynamics in the 3-photon double resonance ionization of phenol via the $S_2$ electronic state", C. P. Schick and P. M. Weber, J. Phys. Chem. A, 105, 3735–3740 (2001)). Moreover, the polarization dependence of the various excitation steps can be considered, and the Rydberg states utilized to measure the energy relaxation dynamics of the model systems. Finally, it has been found that the same ionization pathways exist in molecules unrelated to amino acids, such as cyclohexadiene (see "A 9 eV superexcited state of 1,3-cyclohexadiene revealed by double resonance ionization photoelectron spectroscopy", W. Cheng, C. L. Evans, N. Kuthirummal, P. M. Weber, Chem. Phys. Lett., 349(5,6), 405–410 (2001)).

The lifetime of Rydberg levels increases as $n^3$. Therefore, going to higher Rydberg levels greatly increases the lifetime. Based on studies of typical molecules, the lifetime is expected to be in the range of 1 ns ($10^{-9}$ second) for a value of n of approximately five.

Relatedly, while it makes intuitive sense that larger molecules, where more atom centers scatter the wave function, should have shorter lifetimes, this is not borne out by experimental data. Instead, it has been found that Rydberg states in benzene, for example, have narrower spectral lines, implying longer lifetimes, than those in oxygen molecules.

While it is true that short lifetimes may broaden the bands, it is pointed out that the instrument 10 may employ femtosecond pulsed lasers 32, 34. Thus, even for molecules having lifetimes much faster than typically observed, the instrument 10 is still able to obtain the Rydberg fingerprint data. In fact, the instrument 10 may be designed in view of a worst-case lifetime of $10^{-12}$ s, about three orders of magnitude shorter than typically observed. There is also the further possibility to increase the lifetime by increasing the quantum number.

Thus far the description of this inventon has concentrated on large molecules, such as protein molecules. However, and as was noted earlier, this invention also pertains to nanometer-sized clusters of molecules, such as metallic clusters, and the correlation of specific functionalities of nanometer-sized particles with their composition and structure. An aspect of this invention is the use of the Rydberg states to generate an identifying Rydberg fingerprint of clusters, enabling the identification and segregation of different isomeric cluster forms. A further aspect of this invention is the combination of the Rydberg fingerprinting of clusters with the mass selection of clusters, enabling the separation of isomers of the same mass, and the further identification and separation of clusters exhibiting isomer-specific properties.

In this embodiment of the invention the MALDI source 12 of FIG. 2 is replaced by a suitable cluster source, and the clusters can be cooled by a helium expansion. The skimmed molecular beam intersects the multiple wavelength ionization laser beams 40A and 42A, as was shown in FIG. 4, which prepare specific cluster structures in high Rydberg states. The actual ionization event occurs after some small drift distance in the MATI scheme. Further mass selection, if needed, is accomplished by a quadrupole mass filter (see, for example the quadrupole mass filter 52 in FIG. 14). The clusters are then brought to rest in a reaction chamber by a counter-flowing helium expansion. The catalytic activity of the cluster is probed in a laminar flow reaction chamber by analyzing the reaction products using a conventional mass spectrometer.

There is at present a limited body of knowledge relating to Rydberg levels in small van der Waals clusters. It is known that the spectral shifts upon complexation are on the order of 100 $cm^{-1}$, and dependent on the structure of the cluster. Theoretical studies indicate that, even for reasonably small clusters with, for example, 20 atoms, many thousands of different isomers may exist.

After the clusters are generated in the cluster source 12, such as one described by W. A. de Heer, "The Physics of Simple Metal Clusters: Experimental Aspects and Simple Models", Review of Modem Physics, 65, 611–676 (1993), co-expansion with helium provides for condensation and cooling of the clusters. Clusters of importance include those of nickel, palladium and platinum, which exhibit high catalytic activities.

Figure 13:
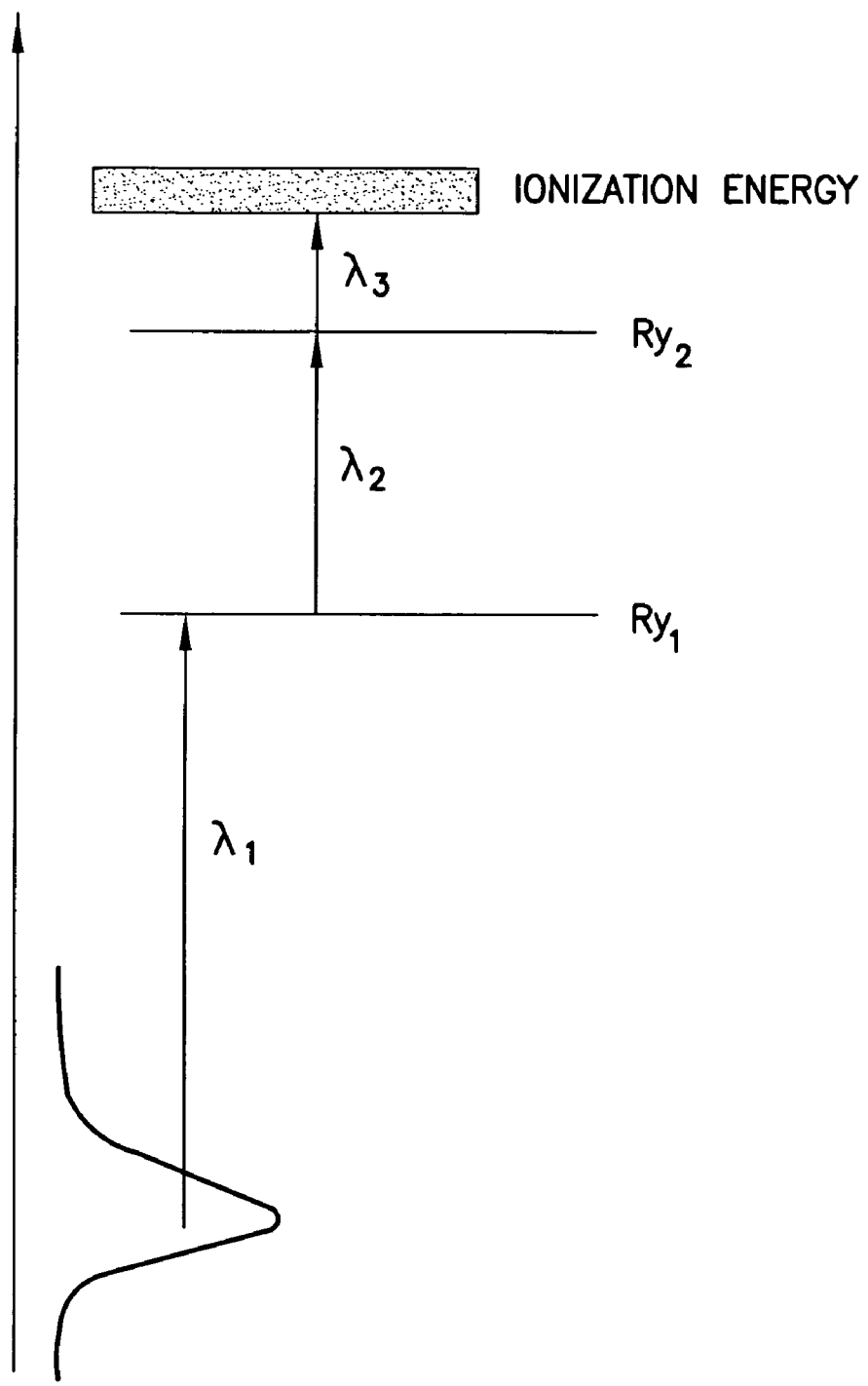
FIG. 13 shows double resonance ionization via the two Rydberg levels, $Ry_1$ and $Ry_2$.

Photoionization is then accomplished in a double resonance, 3-step process, as illustrated in FIG. 13 (similar to FIG. 3). The first step promotes electrons from the highest occupied molecular orbital (in a molecular picture), or the conduction band (in a band theory picture), to the lower Rydberg state $Ry_1$. This Rydberg level can be envisioned as a state with a low principal quantum number, for example, one in the range of from n=3 to n=5.

It has been found that by delaying the pulse 2 and 3 versus pulse 1 it is possible to determine the lifetime, on short time scales, of the cluster isomers. Alternatively, one may tune the third photon to induce a transition from $Ry_1$ to the ionization energy. Tuning the 2nd photon over the spectrum of $Ry_2$ states allows the instrument to identify. cluster size and shape-specific ionization energies. More importantly, from the depletion of the signal from clusters in level 1 it becomes possible to infer which of many $Ry_2$ levels belong to a common cluster structure.

With regard to this photoionization step, it should be noted that the wavelength of the first photon needs only be crudely tunable. The third harmonic of the Titanium Sapphire laser 36 of FIG. 5A is suitable for performing this step. For large clusters, where the band theory picture applies, the energy matching is achieved by capturing an electron with the matching energy from the conduction band. In small clusters, where the molecular orbital approach may be more appropriate, this approach is still valid, without tuning the laser to specific wavelengths, because energy levels lower than the HOMO can be used.

It can further be noted that this step is not specific to either mass or isomeric shape of the cluster. All clusters can be promoted. Also, several Rydberg states may lie within the range of laser excitation.

Further, it is preferable that the laser pulse energy is kept low, so as to minimize the probability for two-photon ionization with two photons of the $\lambda_1$ wavelength. Any ions that are nevertheless created in such a process can be extracted by a small electric field.

A variation of this approach seeks to access $Ry_1$ in a two-step process via an intermediate resonance. Such resonances have been shown to have lifetimes on the order of 3 ps. Since in the illustrative embodiment the laser pulses are of 2 ps duration, this two step process is readily achievable. Such a two step excitation implies tunability of the laser, but would provide a pre-selection of the cluster excitation because the resonances are dependent on the isomeric shape. It should be noted in this regard that the near UV excitations of metal clusters are largely one-electron effects, and that dual excitation of such states will also prepare the desired Rydberg levels via an internal conversion event.

It is further noted that the promotion of the electron to a Rydberg level is associated with a reorganization of the equilibrium structure of the remaining ion core. The transition is sudden, and therefore vertical. This implies that there maybe some amount of vibrational energy inserted in the cluster vibrations. However, any smearing associated with this relaxation into vibrational modes does not affect the Rydberg fingerprint spectroscopy, since the latter is between Rydberg states. Therefore, the energies of Rydberg levels are only weakly dependent on vibrational excitation, and therefore all vertical transitions fall on the same spectral frequency.

Still referring to FIG. 13, the second step promotes the electron from the lower Rydberg state $Ry_1$, to a higher level, $Ry_2$. In this Rydberg-Rydberg transition the angular momentum changes, and therefore the transition frequency depends on the quantum defects of both angular momentum series, as shown in the expression of FIG. 16F.

The third photon prepares the molecule in very high lying Rydberg levels, as commonly done in zero kinetic energy (ZEKE) photoelectron spectroscopy, and Mass Analyzed Threshold Ionization (MATI) spectroscopy. This third transition therefore measures the energy of the $Ry_2$ level, which depends only on the quantum defect $\delta_2$, as shown in FIG. 16G.

This double resonance method measures both energy differences, and therefore the quantum defects of both values can be determined. The preferred ionization approach detects only those clusters that match both transition frequencies. Therefore, any cluster that is generated must simultaneously match both Rydberg fingerprints. This twofold fingerprinting approach greatly enhances the selectivity of the ionization process.

It is noted that one may obtain an indication about how isomer-specific the excitation to $Ry_2$ is by scanning the wavelength of the third photon over the range of ionization energies. Different clusters will give rise to different ionization peaks. If only one isomer is apparent in the Mass Analyzed Threshold Ionization (MATI) spectrum, then it is indicated that selectivity has already been achieved in this intermediate step.

As was noted previously with respect to the protein molecule embodiments, in the MATI approach those ions that are generated directly are extracted by a field. Only those ions that are generated later by a small increased field are observed and contribute to the signal. In this embodiment, then, the final ionic cluster beam contains only those ions that are mass and shape selected.

It is important to note that the photoionization approach employed by this invention does not cause cluster decomposition. While fragmentation of clusters can be observed when using long pulse durations, the optical systems 30A and 30B preferably use laser pulses that are in the range of about 100 femtosecond to about 2 picosecond in duration. These short duration pulses cause negligible fragmentation during the photoionization of both molecules and clusters.

Assuming now by example the use of the laser system of FIG. 5B, and to illustrate the selection of wavelengths, one may consider the case of the nickel clusters. The ionization energies of nickel clusters have been measured by researchers to be around 5.9 eV, depending on cluster size. Choosing as the intermediate resonances the 4s and the 6p states, the following wavelengths (referenced to FIG. 13) can be employed:

$\lambda 1$: <275 nm
$\lambda 2$: 1262 nm
$\lambda 3$: 2858 nm

In order to calculate these wavelengths, which are provided by way of example and not by way of limitation, the quantum defect is assumed to be 0.9 for the s angular momentum state, and 0.4 for the p state.

Referring again to FIG. 5B, the pulse durations of the laser beams 40A and 42A are on the order of 2 ps. The pulses are nearly transform limited, so that the bandwidth is about 10 cm$^{-1}$ FWHM. Depending on the particular Rydberg levels involved, this spectral bandwidth allows a $\delta$ resolution of better than ±0.001.

As was noted above, clusters in various isomeric forms may be generated by condensation processes in the beam. Subsequently, these clusters are ionized in a vertical first step.

An issue arises of maintaining clusters when depositing them on a substrate. Various so-called "soft landing" schemes involve very slow cluster speeds, as well as rare gas matrices to cushion the impact of a cluster on a surface. The soft landing considerations are amplified if one not only desires to preserve cluster mass, but also the isomeric form of the cluster. As the barriers for isomerization are likely to be much smaller than those to fragmentation, an "ultra-soft landing" may be needed to maintain useful isomeric forms. For study of the clusters, one solution is the immersion of the cluster isomers in a bulk gas, rather than the use of deposition on a solid surface. This enables one to characterize the catalytic activity of the cluster, while avoiding the complexity associated with the maintenance of isomeric structures during the soft-landing of the clusters.

Figure 14:
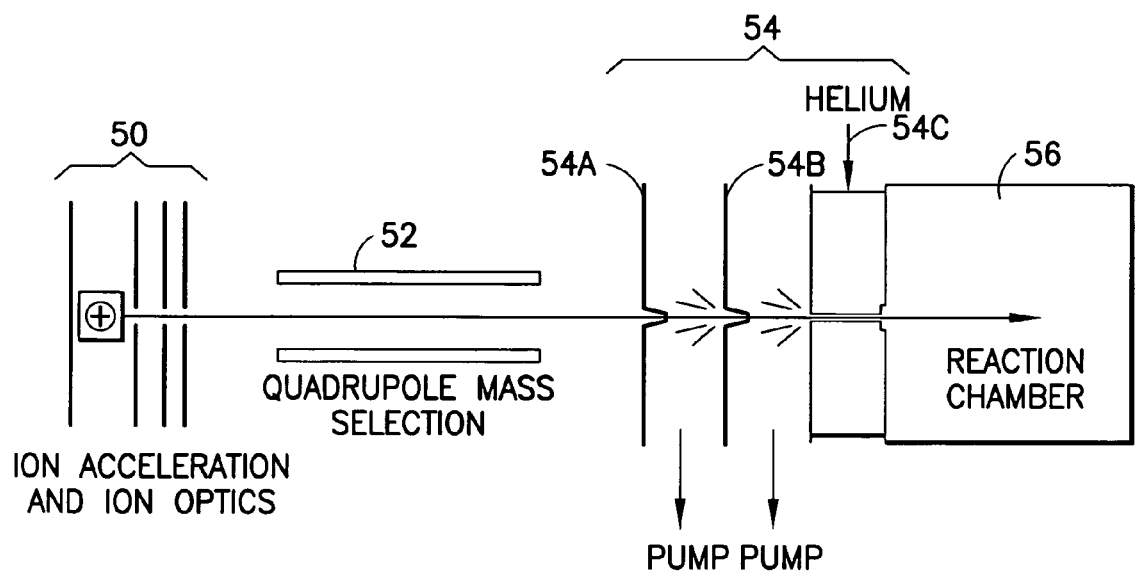
FIG. 14 shows an embodiment of an ultra-soft stopping system, and illustrates the motion of a molecular cluster against a counter-propagating helium beam, and its immersion into a reaction chamber.

A presently preferred approach to this problem is depicted in FIG. 14. The cluster isomer is accelerated by a moderate voltage, for example 10 V, in an ion acceleration and ion optics stage 50. The cluster ions are then passed through a quadrupole mass selection unit 52 and are focused into a counter-propagating helium expansion region 54. The helium itself is expanded in three stages 54A, 54B, 54C from a high pressure (about 1 atm) region to the high vacuum of a reaction chamber 56 by a set of skimmers. The clusters experience a gradually increasing helium pressure, which exerts a friction on its flow. The clusters eventually come to complete rest, at which point they find themselves within the reaction chamber 56, where they can be examined for catalytic activity.

It can be noted that this approach resembles the reverse of an expansion of a cluster by a helium beam. In the case of the expansion, the cluster is accelerated by the helium flow from rest to a velocity approaching that of the helium, e.g., about 1200 m/s, depending on the temperature and cluster mass. Following the initial cooling and condensation, the isomeric form of the cluster is maintained in the latter part of the expansion. The reverse process of stopping the cluster beam with a velocity of about 700 m/s (for about 10 V of kinetic energy, again depending on the cluster mass), operates correspondingly.

Based on simple models of gas/surface accommodation coefficients, the large mass mismatch between the helium gas and the transition metal cluster atoms will result in minimal vibrational excitation of the clusters.

If it were desired to determine the extent of isomerization, and possibly fragmentation, that occurs as a result of the helium drag stopping process shown in FIG. 14, then one may channel the clusters into an attached mass spectrometer. The resulting mass spectrum is then indicative of the extent of fragmentation of the clusters.

If it were desired to determine the degree of isomeric purity (isomeric composition), then one may apply the Rydberg fingerprint spectroscopy discussed above. In this case the clusters are channeled back into the photoionization region and the ultrashort laser pulses are applied to provide the isomerically specific ionization It can be noted that if one were to generate on the order of $10^7$ cluster ions per second, and if the laser system 30A or 30B has a repetition rate of $8 \times 10^7$ pulses per second, the ionization rate corresponds to about one ion every 10 laser pulses. The high repetition rate enables the trapping of on the order of $10^{10}$ clusters in the reaction chamber 56 within about 15 minutes of accumulation time. Expansion of the medium back into the laser interaction region provides adequate signal for the determination of cluster fragments and isomerization events.

Note that various parameters can be adjusted to maximize the survival probability of isomeric cluster forms. These adjustable parameters can include, but need not be limited to, the velocity of the clusters, and the pressure and temperature of the counter-flowing gas. In addition, gas mixtures can be used, such as a mixture of helium with neon.

Having accumulated a population of isomeric clusters, it will often be very desirable to then characterize the catalytic activity of the particular isomer cluster form(s). The prior art approaches to an examination of size-specific catalytic functionality have been performed with clusters soft-landed on substrate surfaces, e.g., soft-landed platinum clusters of specific size on a MgO substrate.

To perform a characterization of catalytic activity of specific cluster isomers, the relevant energy is not the fragmentation energy of the cluster, but rather the energy barriers to isomerization. While the landing of (intact) cluster isomers on substrates is a desirable goal, an aspect of this invention is the characterization of catalytic activity of the clusters in a gaseous environment.

Figure 15:
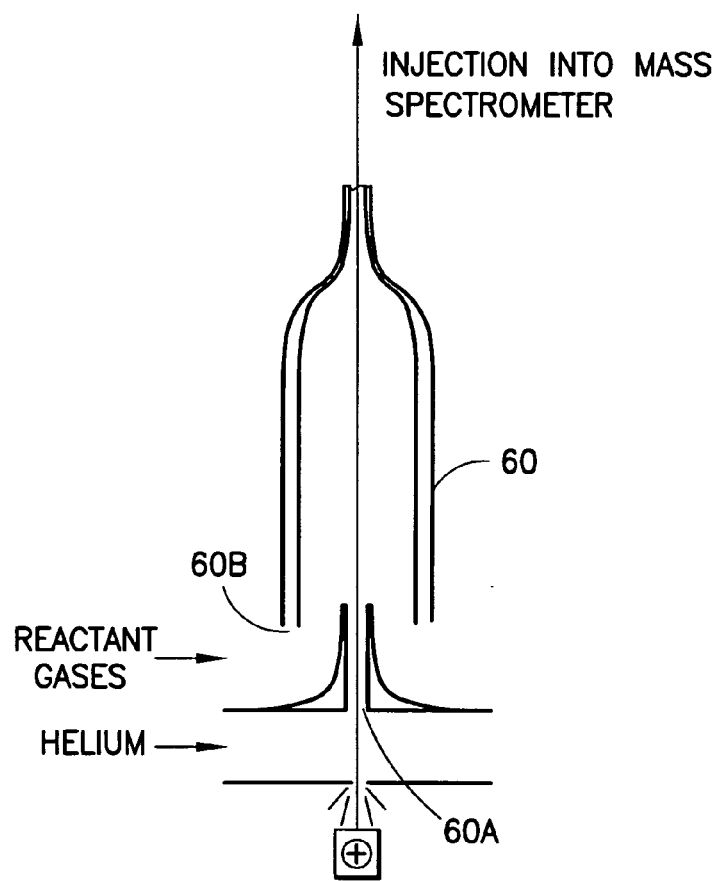
FIG. 15 shows an embodiment of a laminar flow reaction vessel used to determine catalytic activity.

Referring to FIG. 15, in one preferred embodiment the catalytic reaction proceeds in a laminar flow reactor vessel 60 that is fed by the cluster-carrying helium flow at a first port 60A, and by the reactant gas flow at a second port 60B. Laminar flow conditions are desired to minimize condensation of clusters on the walls of the reactor vessel 60. The gas mixtures may then be directly fed to a mass spectrometer (not shown) to analyze the gas composition.

Assuming a cluster flow on the order of $10^7$ clusters per second, the reactant gases may flow at a rate of $10^{18}$ molecules per second, corresponding to a reasonable flow rate of 0.03 Torr 1/s. Assuming that during the residence of a cluster in the reaction vessel 60, about three seconds, there are on the order of 1000 catalytic reactions per cluster, one may reasonably be assumed to observe about $10^{10}$ reaction product molecules per second, corresponding to 10 ppb.

A number of variable parameters can be used to probe the catalytic reaction. Among these are the pressure of the gas mixtures, the temperature of the samples, the flow rate of the reaction mixture, and, most importantly, the isomeric composition of the clusters.

It can be noted that the clusters arrive in the reaction vessel 60 as positive ions, which can be beneficial when characterizing catalysis. In addition, one may inject thermal electrons to neutralize the clusters.

It should be appreciated that the isomer-specific cluster source made possible by the teachings of this invention maybe combined with a number of different instrument types, such as a mass spectrometers as well as an electron diffractometer.

It can be appreciated that the foregoing description has described a technology for separating specific isomeric cluster forms out of a beam containing many cluster sizes and shapes. The technique is general and can be applied to many clusters of interest. The ability to select specific cluster forms is important in many fields of cluster science. For example, one important application is in the field of catalysis, where one is enabled to optimize the catalytic activity of a cluster by tuning its structure. Further applications include, but are not limited to, the design of cluster assembled materials using shape-selected clusters.

It should be further appreciated that the aspects of this invention that pertain to molecules are not limited to protein molecules, but can be applied in general to molecules of a biological origin, as well as to other types of large and complex organic molecules.

Examples include certain complex carbohydrates, such as sugars. Further in this regard, certain amino acids may be separable by exploiting the Rydberg states in accordance with this invention.

It should be further appreciated that the aspects of this invention that pertain to folded proteins can also be applied to advantage to the detection and possible separation of normally folded proteins as well as malformed proteins and incorrectly folded proteins. One example is in the context of prion research and related diagnoses of prion-related or mediated disease states. Another example is in the manufacture of recombinant proteins, where during scale-up from pilot plant to production plant it is important to ensure that the protein product remains correctly folded. Relatedly, this invention could be employed as a quality assurance tool to verify that the product proteins are correctly formed.

This invention can also be used for the detection of the presence of isomers in mixtures, for example, an isomer or isomers mixed with some explosive substance. By adding trace amounts of an isomer or isomers to an explosive it becomes possible to then later determine the source of an explosive substance, a capability that benefits law enforcement.

It can further be realized that this invention can be used in certain cases to detect and separate optical isomers, i.e., those exhibiting left and right handedness. This is particularly true where the color center/ion core is physically separate from the remainder of the molecule.

Based on the foregoing discussion it should be appreciated that instruments that are constructed in accordance with this invention are scalable in complexity and functionality over a wide range. For example, at one end of the spectrum are instruments designed to detect the presence of a single type (or family) of molecules or clusters, and in this case the optical excitation system and detector are simplified and optimized for this one specific use. For example, low cost laser diodes may be employed, as can small detectors placed at fixed locations. Examples of such instruments are those designed to detect the presence of a specific type of molecule, such as a protein, in blood, urine or spinal fluid. At the other end of the spectrum are large instruments designed for laboratory experimental use with a wide range of molecules and/or clusters. These types of instruments may use multiple tunable optical sources, multiple large area detectors, and may be used to provide an input to other types of analytical instruments, such as mass spectrometers and electron diffractometers.

It can be further appreciated that this invention can be employed solely as a means to separate and segregate a specific isomer form of a molecule or cluster from others isomers. For example, when detecting the arrival of an electron at a specific pixel of the detector 22 shown in FIG. 4, indicating the presence of a desired isomer, a deflection grid can be briefly energized to divert the isomer, having a desired mass, to a desired collection location, such as a substrate.

Thus, while disclosed herein in the context of presently preferred embodiments of this invention, those having skill in the art should appreciate that changes in detail and form may be made to these embodiments, and that equivalent methods and apparatus may be employed, and that all such changes, modifications and equivalents will still fall within the scope of this invention.

What is claimed is:

1. A method to characterize a shape of an isomeric form of a sample comprised of a molecule or a cluster of molecules, comprising:
    raising an electron of the sample to a Rydberg state having an orbital diameter sufficient to encompass at least a portion of the sample;
    further raising the electron to an ionization state; and
    correlating the energy required to transition from the Rydberg state to the ionization state with the three dimensional structure of the sample.

2. A method as in claim 1, where further raising the electron to the ionization state comprises raising the electron from the Rydberg state to the ionization state using optical excitation, and where correlating considers at least a wavelength of the optical excitation.

3. A method as in claim 1, where raising the electron to the Rydberg state comprises raising the electron to a first Rydberg state $Ry_1$, and raising the electron to a second Rydberg state $Ry_2$, where further raising the electron to the ionization state comprises raising the electron from the $Ry_2$ state to the ionization state using optical excitation, and where correlating considers at least a wavelength of the optical excitation.

4. A method as in claim 1, where the sample comprises a protein molecule.

5. A method as in claim 1, where the sample comprises a metallic cluster.

6. A method to characterize a shape of an isomeric form of a sample comprised of a molecule or a cluster of molecules, comprising:
    raising an electron of the sample to a Rydberg state having an orbital diameter sufficient to encompass at least a portion of the sample;
    further raising the electron to an ionization state; and
    correlating the energy required to transition from the Rydberg state to the ionization state with the three dimensional structure of the sample, further comprising determining a mass of the sample using a mass spectrometer.

7. A method to separate at least one isomeric form of a sample from other isomeric forms of the sample, where the sample is comprised of a molecule or a cluster of molecules, comprising:
    raising an electron of the sample to a Rydberg state having an orbital diameter sufficient to encompass at least a portion of the sample;
    further raising the electron to an ionization state;
    identifying the desired isomeric form of the sample from the energy required to transition from the Rydberg state to the ionization state; and
    in response to identifying the desired isomeric form of the sample, physically segregating the identified sample having the desired isomeric form from other samples having other isomeric forms.

8. A method as in claim 7, where further raising the electron to the ionization state comprises raising the electron from the Rydberg state to the ionization state using optical excitation, and where identifying considers at least a wavelength of the optical excitation.

9. A method as in claim 7, where raising the electron to the Rydberg state comprises raising the electron to a first Rydberg state $Ry_1$, and raising the electron to a second Rydberg state $Ry_2$, where further raising the electron to the ionization state comprises raising the electron from the $Ry_2$ state to the ionization state using optical excitation, and where identifying considers at least a wavelength of the optical excitation.

10. A method as in claim 7, where the samples comprise protein molecules.

11. A method as in claim 7, where the samples comprise metallic clusters.

12. A method as in claim 7, where segregating comprises deflecting the desired isomeric form of the sample from a sample stream, and further comprising collecting the deflected samples.

13. Apparatus to characterize a shape of an isomeric form of a sample comprised of a molecule or a cluster of molecules, comprising:
    an optical excitation system for raising an electron of the sample to a Rydberg state having an orbital diameter sufficient to encompass at least a portion of the sample, and for further raising the electron to an ionization state; and
    means for correlating the energy required to transition from the Rydberg state to the ionization state with the three dimensional structure of the sample.

14. Apparatus as in claim 13, where said correlating means considers at least a wavelength of the optical excitation.

15. Apparatus as in claim 13, where said optical excitation system generates multiple outputs for raising the electron to a first Rydberg state $Ry_1$ and for raising the electron to a second Rydberg state $Ry_2$, and for raising the electron from the $Ry_2$ state to the ionization state, and where said correlating means considers at least a wavelength of the optical excitation.

16. Apparatus as in claim 13, where the sample comprises a protein molecule.

17. Apparatus as in claim 13, where the sample comprises a metallic cluster.

18. Apparatus to characterize a shape of an isomeric form of a sample comprised of a molecule or a cluster of molecules, comprising:
    an optical excitation system for raising an electron of the sample to a Rydberg state having an orbital diameter sufficient to encompass at least a portion of the sample, and for further raising the electron to an ionization state; and
    means for correlating the energy required to transition from the Rydberg state to the ionization state with the three dimensional structure of the sample, further comprising means for determining a mass of the sample.

19. Apparatus to separate at least one isomeric form of a sample from other isomeric forms of the sample, where the sample is comprised of a molecule or a cluster of molecules, comprising:
    an optical excitation system for raising an electron of the sample to a Rydberg state having an orbital diameter sufficient to encompass at least a portion of the sample, and for further raising the electron to an ionization state;
    means for identifying the desired isomeric form of the sample from the energy required to transition from the Rydberg state to the ionization state; and
    means, responsive to identifying the desired isomeric form of the sample, for physically segregating the identified sample having the desired isomeric form from other samples having other isomeric forms.

20. Apparatus as in claim 19, where said means for identifying considers at least a wavelength of the optical excitation.

21. Apparatus as in claim 19, where said optical excitation system generates multiple outputs for raising the electron to a first Rydberg state $Ry_1$ and for raising the electron to a second Rydberg state $Ry_2$, and for raising the electron from the $Ry_2$ state to the ionization state, and where said identifying means considers at least a wavelength of the optical excitation.

22. Apparatus as in claim 19, where the samples comprise protein molecules.

23. Apparatus as in claim 19, where the samples comprise metallic clusters.

24. Apparatus as in claim 19, where said segregating means comprises means for deflecting the desired isomeric form of the sample from a sample stream, and further comprising means for collecting the deflected samples.

25. A method to detect an isomeric form of a sample comprised of a molecule or a cluster of molecules, comprising:
  providing a sample stream comprised of a population of sample ions, said population of sample ions comprising a plurality of isomeric forms of the sample;
  applying first optical excitation for raising electrons of individual sample ions of the sample stream to at least one Rydberg state having an orbital diameter that encompasses at least a portion of the sample ion;
  applying second optical excitation for raising the electrons from the Rydberg state to an ionization state, thereby generating photoelectrons; and
  responsive to detecting at least one photoelectron, correlating at least a wavelength of the second optical excitation with a predetermined isomeric form of the sample.

26. A method as in claim 25, further comprising at least one of segregating sample ions having the predetermined isomeric form from the sample stream and determining a mass of sample ions having the predetermined isomeric form.

27. A method as in claim 25, where applying first optical excitation raises the electrons to a first Rydberg state $Ry_1$ and then to a second Rydberg state $Ry_2$, where applying the second optical excitation raises the electrons from the $Ry_2$ state to the ionization state.

28. A method as in claim 25, where the sample stream comprises protein molecules or constituents thereof.

29. A method as in claim 25, where the sample stream comprises clusters that comprise at least one metal.

30. A method as in claim 25, where applying first and second optical excitation comprises establishing a wavelength gradient region through which said sample stream passes, and where correlating comprises detecting an arrival of a photoelectron from a particular location within the wavelength gradient region with a particular wavelength that caused a transition from the Rydberg state to the ionization state.

31. A method as in claim 30, where establishing the wavelength gradient region comprises applying pulses of spectrally dispersed first laser light and pulses of spectrally dispersed second laser light to a region of space through which said sample stream passes, where the spectrally dispersed first laser light comprises at least one wavelength for causing electrons to transition from a first Rydberg state $Ry_1$ to a second Rydberg state $Ry_2$, and where the spectrally dispersed second laser light comprises at least one wavelength for causing electrons to transition from the $Ry_2$ state to the ionization state.

32. A method as in claim 31, where the pulses of spectrally dispersed first laser light and the pulses of spectrally dispersed second laser light are applied substantially orthogonally to one another.

33. A method as in claim 25, where said at least one Rydberg state is characterized by a principal quantum number in the range of about 3 to about 15.

34. Apparatus to detect an isomeric form of a sample comprised of a molecule or a cluster of molecules, comprising:
  a sample stream generator providing a sample stream comprised of a population of sample ions, said population of sample ions comprising a plurality of isomeric forms of the sample;
  an optical system for applying first optical excitation for raising electrons of individual sample ions of the sample stream to at least one Rydberg state having an orbital diameter that encompasses at least a portion of the sample ion, and for applying second optical excitation for raising the electrons from the Rydberg state to an ionization state, thereby generating photoelectrons; and
  a detector system, responsive to photoelectrons, for correlating at least a wavelength of the second optical excitation with a predetermined isomeric form of the sample.

35. Apparatus as in claim 34, further comprising means for at least one of segregating sample ions having the predetermined isomeric form from the sample stream and determining a mass of sample ions having the predetermined isomeric form.

36. Apparatus as in claim 34, said optical system operates for applying the first optical excitation to raise the electrons to a first Rydberg state $Ry_1$ and then to a second Rydberg state $Ry_2$, an further operates for applying the second optical excitation to raise the electrons from the $Ry_2$ state to the ionization state.

37. Apparatus as in claim 34, where the sample stream comprises protein molecules or constituents thereof.

38. Apparatus as in claim 34, where the sample stream comprises clusters that comprise at least one metal.

39. Apparatus as in claim 34, where said optical system comprises means for establishing a wavelength gradient region through which said sample stream passes, and where said detector system detects an arrival of a photoelectron from a particular location within the wavelength gradient region and correlates the particular location with a particular wavelength that caused a transition from the Rydberg state to the ionization state.

40. Apparatus as in claim 39, where said means for establishing the wavelength gradient region comprises means for applying pulses of spectrally dispersed first laser light and pulses of spectrally dispersed second laser light to a region of space through which said sample stream passes, where the spectrally dispersed first laser light comprises at least one wavelength for causing electrons to transition from a first Rydberg state $Ry_1$ to a second Rydberg state $Ry_2$, and where the spectrally dispersed second laser light comprises at least one wavelength for causing electrons to transition from the $Ry_2$ state to the ionization state.

41. Apparatus as in claim 40, where the pulses of spectrally dispersed first laser light and the pulses of spectrally dispersed second laser light are applied substantially orthogonally to one another.

42. Apparatus as in claim 34, where said at least one Rydberg state is characterized by a principal quantum number in the range of about 3 to about 15.

43. Apparatus to characterize a sample comprised of a plurality of molecules or clusters of molecules, comprising:
sample stream generator means providing a sample stream comprised of a population of sample ions, said population of sample ions comprising a plurality of isomeric forms of the sample;
excitation means for raising a sample ion electron to at least one Rydberg state having an orbital diameter that encompasses at least a portion of the sample ion, and for raising the sample ion electron from the at least one Rydberg state to an ionization state; and
detector means, responsive to the sample ion electron being raised to the ionization state, for detecting the presence of a certain isomeric form of the sample.

44. Apparatus as in claim 43, where the sample comprises molecules of a biological origin.

45. Apparatus as in claim 43, where the sample comprises a protein, and where the certain isomeric form of the sample comprises one of a correctly folded or a misfolded form of the protein.

46. Apparatus as in claim 43, where the certain isomeric form of the sample comprises a predetermined optical isomeric form of the sample.

47. Apparatus as in claim 43, where the sample comprises a cluster of metal molecules, and where the certain isomeric form of the sample comprises a cluster of metal molecules having a certain catalytic activity.

48. Apparatus to characterize a sample comprised of a plurality of molecules or clusters of molecules, comprising:
sample stream generator means providing a sample stream comprised of a population of sample ions, said population of sample ions comprising a plurality of isomeric forms of the sample;
excitation means for raising a sample ion electron to at least one Rydberg state having an orbital diameter that encompasses at least a portion of the sample ion, and for raising the sample ion electron from the at least one Rydberg state to an ionization state; and
detector means, responsive to the sample ion electron being raised to the ionization state, for detecting the presence of a certain isomeric form of the sample, further comprising means for determining the mass of the certain isomeric form of the sample.

49. Apparatus as in claim 43, further comprising means for segregating molecules or clusters of molecules having the certain isomeric form of the sample from molecules or clusters of molecules that do not have the certain isomeric form of the sample.

50. Apparatus to characterize a sample comprised of a plurality of molecules or clusters of molecules, comprising:
sample stream generator means providing a sample stream comprised of a population of sample ions, said population of sample ions comprising a plurality of isomeric forms of the sample;
excitation means for raising a sample ion electron to at least one Rydberg state having an orbital diameter that encompasses at least a portion of the sample ion, and for raising the sample ion electron from the at least one Rydberg state to an ionization state;
detector means, responsive to the sample ion electron being raised to the ionization state, for detecting the presence of a certain isomeric form of the sample; and
means for segregating molecules or clusters of molecules having the certain isomeric form of the sample from molecules or clusters of molecules that do not have the certain isomeric form of the sample,
where the certain isomeric form of the sample comprises molecules or clusters of molecules having a certain catalytic activity, and further comprising means for characterizing the catalytic activity of segregated molecules or clusters of molecules.

51. Apparatus as in claim 49, further comprising means for collecting the segregated molecules or clusters of molecules.

52. A method, comprising:
applying first optical excitation to raise an electron of at least one molecule to a Rydberg state having an orbital diameter sufficient to encompass at least a portion of the at least one molecule;
applying second optical excitation to transition the electron from the Rydberg state to an ionization state; and
correlating the energy required to transition from the Rydberg state to the ionization state with a shape of the at least one molecule.

53. A method as in claim 52, where correlating considers at least a wavelength of the optical excitation.

54. A method as in claim 52, where the at least one molecule comprises am organic molecule.

55. A method as in claim 52, where the at least one molecule comprises a metallic cluster.

56. A method as in claim 52, where applying first optical excitation and applying second optical excitation comprises sending the at least one molecule through a wavelength gradient region, and where correlating comprises spatially detecting a location within the wavelength gradient region where the electron transitions from the Rydberg state to the ionization state.

57. A method as in claim 52, where the at least one molecule comprises a cluster of molecules, further comprising characterizing activity of the cluster of molecules in a gaseous environment.

58. A method as in claim 52, where the at least one molecule comprises a cluster of metal-containing molecules, further comprising characterizing catalytic activity of the cluster of metal-containing molecules in a gaseous environment.

59. A method as in claim 52, where correlating further comprises distinguishing a first isomer of the at least one molecule from at least one other isomer of the at least one molecule.

60. A method as in claim 59, where the first isomer and the at least one other isomer comprise optical isomers.

61. A method as in claim 52, where the at least one molecule comprises a cluster of molecules, further comprising separating the cluster of molecules into a flow comprised of the cluster of molecules, and exerting friction on the flow to bring the flow to rest within an analysis chamber.

62. A method as in claim 61, where the cluster of molecules comprises a cluster of metal-containing molecules, further comprising characterizing catalytic activity of the cluster of metal-containing molecules within the analysis chamber.

63. Apparatus, comprising:
means for applying first optical excitation to raise an electron of at least one molecule to a Rydberg state having an orbital diameter sufficient to encompass at least a portion of the at least one molecule;
means for applying second optical excitation to transition the electron from the Rydberg state to an ionization state; and means for correlating the energy required to transition from the Rydberg state to the ionization state with a shape of the at least one molecule.

64. Apparatus as in claim 63, where correlating considers at least a wavelength of the optical excitation.

65. Apparatus as in claim 63, where the at least one molecule comprises am organic molecule.

66. Apparatus as in claim 63, where the at least one molecule comprises a metallic cluster.

67. Apparatus as in claim 63, where said means for applying first optical excitation and for applying second optical excitation comprise means for sending the at least one molecule through a wavelength gradient region, and where said correlating means comprises means for spatially detecting a location within the wavelength gradient region where the electron transitions from the Rydberg state to the ionization state.

68. Apparatus as in claim 63, where the at least one molecule comprises a cluster of molecules, further comprising means for characterizing activity of the cluster of molecules in a gaseous environment.

69. Apparatus as in claim 63, where the at least one molecule comprises a cluster of metal-containing molecules, further comprising means for characterizing catalytic activity of the cluster of metal-containing molecules in a gaseous environment.

70. Apparatus as in claim 63, where said correlating means further comprises means for distinguishing a first isomer of the at least one molecule from at least one other isomer of the at least one molecule.

71. Apparatus as in claim 70, where the first isomer and the at least one other isomer comprise optical isomers.

72. Apparatus as in claim 63, where the at least one molecule comprises a cluster of molecules, further comprising means for separating the cluster of molecules into a flow comprised of the cluster of molecules, and means for exerting friction on the flow to bring the flow to rest within an analysis chamber.

73. Apparatus as in claim 72, where the cluster of molecules comprises a cluster of metal-containing molecules, further comprising means for characterizing catalytic activity of the cluster of metal-containing molecules within the analysis chamber.

* * * * *